US006372215B1

(12) United States Patent
Starling et al.

(10) Patent No.: US 6,372,215 B1
(45) Date of Patent: Apr. 16, 2002

(54) MONOCLONAL ANTIBODIES TO HUMAN CD6

(75) Inventors: Gary C. Starling, Lawrenceville, NJ (US); Anthony W. Siadak, Seattle, WA (US); Michael A. Bowen, Princeton; Alejandro A. Aruffo, Belle Mead, both of NJ (US); Jurgen Bajorath, Lynnwood, WA (US); Dale L. Bodian, Paoli, PA (US); John E. Skonier, Seattle, WA (US)

(73) Assignee: Bristol-Myers Squibb Company, New York, NY (US)

( * ) Notice: Subject to any disclaimer, the term of this patent is extended or adjusted under 35 U.S.C. 154(b) by 0 days.

(21) Appl. No.: 09/030,182

(22) Filed: Feb. 25, 1998

Related U.S. Application Data

(60) Provisional application No. 60/040,016, filed on Mar. 3, 1997.

(51) Int. Cl.[7] ...................... A61K 39/395; A61K 39/00; C12P 21/04; G01N 33/53; C07K 16/00
(52) U.S. Cl. ................. 424/141.1; 424/130.1; 424/133.1; 424/134.1; 424/178.1; 424/801; 435/70.1; 435/70.2; 435/70.25; 436/548; 532/350; 532/386; 532/387.1; 532/388.1; 532/391.1; 532/808; 532/864
(58) Field of Search .......................... 424/133.1, 141.1, 424/178.1, 801, 134.1, 130.1; 435/70.1, 70.2, 70.21; 436/548; 530/350, 386, 387.1, 388.1, 391.1, 808, 864

(56) References Cited

U.S. PATENT DOCUMENTS 5,968,768 A  * 10/1999  Haynes et al. .............. 435/69.1

FOREIGN PATENT DOCUMENTS

| EP | 0239400 | * | 9/1987 |
| WO | PCT/GB/02017 | * | 7/1991 |

OTHER PUBLICATIONS

Rudikoff etal ; P.N.A.S; vol. 79; 1979–1983, 1982.*
Panka et al; P.N.A.S; vol. 85; 3080–3084, 1988.*
Amit et al; Science vol. 233; 747–753, 1986.*
Riechmann et al; Nature; vol. 332; 323–327, 1988.*
Queen et al; PNAS; vol. 86; 10029–10033, 1996.*
Kirkman et al., "Treatment of Acute Renal Allograft Rejection with Monoclonal Anti–T12 Antibody," *Transplantation* 36:620–626 (1983).
Queen et al., "Cell–Type Specific Regulation of a κ Immunoglobulin Gene by Promoter and Enhancer Elements," *Immunol. Review,* 89:49–68 (1986).
Hafler et al., "Immunologic Responses of Progressive Multiple Sclerosis Patients treated with an anti–T–cell monoclonal antibody, anti–T12," *Neurology* 36:777–784 (1986).
Jones et al., "Isolation of complementary DNA clones encoding the human lymphocyte glycoprotein T1/Leu–1," *Nature* 323:346–349 (1986).
Goldberger et al., "Human Complement Factor I: Analysis of cDNA–derived Primary Structure and Assignment of Its Gene to Chromosome 4," *J. Biol. Chem.* 262:10065–10071 (1987).
Morimoto et al., "2H1—A Novel Antigen Involved in T Lymphocyte Triggering," *J. Immunol.* 140:2165–2170 (1988).
Gangemi et al., "Anti–T12, An Anti–CD6 Monoclonal Antibody, Can Activate Human T Lympocytes," *J. Immunol.* 143:2439–2447 (1989).
Mayer et al., "Expression of the CD6 T Lymphocyte Differentiation Antigen in Normal Human Brain," *J. Neuroimmunol.* 29:193–202 (1990).
Cardenas et al., "Phosphorylation–Dephosphorylation of the CD6 Glycoprotein Renders Two Isoforms of 130 and 105 Kilodaltons," *J. Immunol.* 145:1450–1455 (Sep. 1, 1990).
Swack et al., "Biosynthesis and Post–translational Modification of CD6, a T Cell Signal–transducing Molecule," *J. Biol. Chem.,* 266:7137–7143 (1991).
Matsumoto et al., "Intersection of the Complement and Immune Systems: A Signal Transduction Complex of the B Lymphocyte–containing Complement Receptor Type 2 and CD19," *J. Exp. Med.* 173:55–64 (1991).
Tanaka et al., "Molecular Cloning and Expression of a Novel Adhesion Molecule, SC1," *Neuron* 7:535–545 (Oct., 1991).
Burns et al., "DM–GRASP, a Novel Immunoglobulin Superfamily Axonal Surface Protein That Supports Neurite Extension," *Neuron* 7:209–220 (Aug., 1991).
Corbel et al., "An Antigen Expressed by Avian Neuronal Cells is also Expressed by Activated T Lymphocytes," *Cell. Immunol.* 141:99–110 (1992).
Co et al., Chimeric and Humanized Antibodies with Specificity for the CD33 Antigen, *J. Immunol.* 148:1149–1154 (Feb. 15, 1992).
Pourquie et al., "BEN, a Surface Glycoprotein of the Immunoglobulin Superfamily, is Expressed in a Variety of Developing Systems," *Proc. Natl. Acad. Sci. USA* 89:5261–5265 (Jun., 1992).
Soiffer et al., "Prevention of Graft–Versus–Host Disease by Selective Depletion of CD6–Positive T Lymphocytes from Donor Bone Marrow," *J. Clin. Oncol.* 10:1191–1200 (Jul., 1992).
Wijngaard et al., "Molecular Characterization of the WC1 Antigen Expressed Specifically on Bovine $CD4^-CD8^-$ γδ T Lymphocytes," *J. Immunol.* 149:3273–3277 (Nov. 15, 1992).

(List continued on next page.)

*Primary Examiner*—Mark Navarro
*Assistant Examiner*—Padma Baskar
(74) *Attorney, Agent, or Firm*—Townsend and Townsend and Crew LLP

(57) ABSTRACT

The invention provides antibodies and other binding agents that bind specifically to SRCR domains of human CD6 (hCD6) and have advantageous properties, including the capacity to substantially inhibit binding of activated leukocyte adhesion molecule (ALCAM) to hCD6. The binding agents of the invention are useful, inter alia, in methods for screening peptides and drugs that also bind to hCD6 and/or modulate ALCAM binding to hCD6, as well as in diagnostic and therapeutic methods for management and treatment of inflammatory and autoimmune diseases.

16 Claims, 12 Drawing Sheets

OTHER PUBLICATIONS

Law et al., "A New Macrophage Differentiation Antigen Which is a Member of the Scavenger Receptor Superfamily," *Eur. J. Immunol.* 23:2320–2325 (1993).

Bott et al., "Activation of Human T Cells Through CD6: Functional Effects of a Novel Anti–CD6 Monoclonal Antibody and Definition of Four Epitopes of the CD6 Glycoprotein," *Int. Immunol.* 5:783–792 (1993).

Wee et al., "Tyrosine Phosphorylation of CD6 by Stimulation of CD3: Augmentation by the CD4 and CD2 Coreceptors," *J. Exp. Med.* 177:219–223 (Jan., 1993).

Friedman et al., "Cloning and Characterization of Cyclophilin C–associated Protein: A Candidate Natural Cellular Ligand for Cyclophilin C," *Proc. Natl. Acad. Sci. USA* 90:6815–6819 (Jul., 1993).

Resnick et al., "The SRCR Superfamily: A Family Reminiscent of the Ig Superfamily," *Trends Biochem. Sci.* 19:5 (1994).

Osorio et al., "The Anti–CD6 mAb, IOR–T1, Defined a New Epitope on the Human CD6 Molecule That Induces Greater Responsiveness in T Cell Receptor/CD3–Mediated T Cell Proliferation," *Cell. Immunol.* 154:123–133 (1994).

Peduzzi et al., "Distribution and Characteristics of a 90 kDa Protein, KG–CAM, in the Rat CNS," *Brain Res.*, 640:296–307 (1994).

Anderson et al., "Acute Kidney Graft Rejection," *APMIS* 102:23–27 (1994).

Bowen et al., "Cloning, Mapping and Characterization of Activated Leukocyte–Cell Adhesion Molecule (ALCAM) a CD6 Ligand," *J. Exp. Med.,* 181:2213–2220 (Jun. 1995).

Yang et al., "Prolongation of Rate Islet Allograft Survival by Treatment with Monoclonal Antibodies Against VLA–4 and LFA–1," *Transplantation* 60:71–76 (Jul. 15, 1995).

Schlegel et al., "Inhibition of T Cell Costimulation VCAM–1 Prevents Murine Graft–Versus–Host Disease Across Minor Histocompatibility Barriers" *J. Immunol.* 155:3856–3865 (1995).

Bajorath et al., "Molecular Model of the N–terminal Receptor–binding Domain of the Human CD6 Ligand ALCAM," *Protein Science* 4:1644–1647 (1995).

Whitney et al., "The Membrane–Proximal Scavenger Receptor Cysteine–rich Domain of CD6 Contains the Activated Leukocyte Cell Adhesion Molecule Binding Site," *J. Biol. Chem.* 270:18187–18190 (1995).

Corbel et al., "BEN/SC1/DM–GRASP, a Homophilic Adhesion Molecule, is Required for In Vitro Myeloid Colony Formation by Avian Hemopoietic Progenitors," *Proc. Natl. Acad. Sci. USA* 93:2844–2849 (Apr., 1996).

Starling et al., "Characterization of Mouse CD6 with Novel Monoclonal Antibodies which Enhance the Allogeneic Mixed Leukocyte Reaction," *Eur. J. Immunol.* 26:738–746 (1996).

DeBarnardo and Chang, "Heterophilic Interactions of DM–GRASP: GRASP–NgCAM Interactions Involved in Neurite Extension," *J. Cell. Biol.* 133:657–666 (1996).

Skonier et al., "Recognition of Diverse Proteins by Members of the Immunoglobulin Superfamily: Delineation of the Receptor Binding Site in the Human CD6 Ligand ALCAM," *Biochem.* 35:12287–12291 (1996).

Bowen et al., "The Amino–terminal Immunoglobulin–like Domain of Activated Leukocyte Cell Adhesion Molecule Binds Specifically to the Membrane–proximal Scavenger Receptor Cysteine–rich Domain of CD6 with a 1:1 Stoichiometry," *J. Biol. Chem.* 271:17390–17396 (1996).

Singer et al., "Role of the CD6 Glycoprotein in Antigen–specific and Autoreactive Responses of Cloned Human T Lymphocytes," *Immunol.* 88:537–543 (1996).

Skonier et al., "Mutational Analysis of the CD6 Binding Site in Activated Leukocyte Cell Adhesion Molecule," *Biochem.* 35:14743–14748 (1996).

Paul et al., "Anti–integrin (LFA–1, VLA–4, and Mac–1) Antibody Treatment and Acute Cardiac Graft Rejection in the Rat," *Transpl. Int.* 9:420–425 (1996).

Gorczynski et al., "Altered Patterns of Migration of Cytokine–Producing T Lymphocytes in Skin–Grafted Naive or Immune Mice Following in vivo Administration of Anti–VCAM–1 or –ICAM–1," *Immunol.* 87:573–580 (1996).

\* cited by examiner

MONOCLONAL ANTIBODIES TO HUMAN CD6

This application claims benefit to U.S. provisional application Ser. No. 60/040,016, filed Mar. 3, 1997.

BACKGROUND OF THE INVENTION

CD6 is an important cell surface protein predominantly expressed by human T cells and a subset of B cells, as well as by some B cell chronic lymphocytic leukemias and neurons (see, e.g., Aruffo et al., *J. Exp. Med.*, 174:949 (1991); Kamoun et al., *J. Immunol.* 127:987 (1981); Mayer et al., *J. Neuroimmunol.* 29:193 (1990)). CD6 is a member of a large family of proteins characterized by having at least one domain homologous to the scavenger receptor cysteine-rich domain (SRCR) of type I macrophages (Matsumoto, et al., *J. Exp. Med.*, 173:55 (1991) and Resnick et al., *Trends Biochem. Sci.*, 19:5 (1994)). Other members of this family include CD5 (Jones et al., *Nature*, 323:346 (1986); cyclophilin C (Friedman et al., *PNAS* 90:6815 (1993)); complement factor I, which binds activated complement proteins C3b and C4b (Goldberger, et al., *J. Biol. Chem.*, 262:10065 (1987)); bovine WC-1 expressed by τ/δ T cells (Wijingaard et al., *J. Immunol.*, 149:3273 (1992)); and M130 (Law et al., *Eur J. Immunol.*, 23:2320 (1993)), a macrophage activation marker.

Blocking studies using anti-CD6 monoclonal antibodies (mAbs) suggest that CD6 plays an important role in T cell development by regulating T cell adhesive interactions with thymic epithelial (TE) cells (Patel et al., *J. Exp. Med.* 181:1563–1568 (1995)). Additional studies have shown that CD6 can function as an important accessory molecule in T cell activation. For example, certain anti-CD6 mAb are directly mitogenic for T cells (Gangemi et al., *J. Immunol.*, 143:2439 (1989) and Bott et al., *Int. Immunol.* 7:783 (1993), whereas others are able to co-stimulate T cell proliferation in conjunction with anti-CD3, anti-CD2 or PMA (Gangemi et al., *J. Immunol.*, 143:2439 (1989); (Morimoto et al., *J. Immunol.*, 140:2165–2170 (1988); and (Osorio et al., *Cell. Immunol.*, 154:23 (1994)). Yet additional evidence of the role of CD6 in T cell activation comes from studies showing that CD6 becomes hyperphosphorylated on Ser and Thr residues (Swack et al., *Mol. Immunol.* 26:1037–1049 (1989); Swack et al., *J. Biol. Chem.* 266:7137 (1991); Cardenas et al., *J. Immunol.*, 145:1450–1455 (1990)) and phosphorylated on Tyr residues (Wee et al., *J. Exp. Med.*, 177:219–223 (1993)) following T cell activation. These and other studies implicate CD6 as an important modulator of both immature and mature T cell function in vivo, affecting both T cell activation and signal transduction.

The extracellular domain of the mature CD6 protein is composed of three SRCR domains (hereinafter designated CD6D1, CD6D2, and CD6D3, with CD6D3 corresponding to the membrane proximal SRCR domain) followed by a short 33-amino-acid stalk region. These extracellular domains are anchored to the cell membrane via a short transmembrane domain followed by a cytoplasmic domain of variable length (Aruffo et al., *J. Exp. Med.*, 174:949 (1991)).

Studies using CD6-immunoglobulin fusion proteins, containing selected extracellular domains of CD6 fused to human IgG$_1$ constant domains (CD6-Rgs), led to the identification and cloning of a CD6 ligand, designated "activated leukocyte cell adhesion molecule" (ALCAM) (Wee, et al., *Cell. Immunol.*, 158:353–364, (1994); Patel, et al., *J. Exp. Med.* 181:1563–1568 (1995); Bowen et al., *J. Exp. Med.*, 181:2213–2220 (1995). ALCAM is a member of the immunoglobulin supergene family and may be a human homologue of the chicken neural adhesion molecule BEN/SC-1/DM-GRASP (Pourquie et al., *PNAS*, 89:5261–5265 (1992); Tanaka et al., *Neuron*, 535–545 (1991); and Burns et al., *Neuron*, 209–220 (1991)) and the rat protein KG-CAM (Peduzzi et al., *Brain Res.*, 640:296–307 (1994)). In the chicken, BEN/SC-1/DM-GRASP is able to mediate homophilic interactions, and has been shown to be involved in neurite outgrowth in the nervous system.

In addition to being expressed by neurons, ALCAM is expressed by human TE cells and a variety of other cell types (Patel et al., *J. Exp. Med.*, 181:1563 (1995)) and transiently expressed by activated leukocytes (Bowen et al., *J. Exp. Med.*, 181:2213 (1995)). Notably, cell adhesion assays demonstrated that CD6-ALCAM interactions are in part responsible for mediating thymocyte binding to TE cells (Bowen et al., *J. Exp. Med.*, 181:2213–2220 (1995)). Analysis of the in vitro kinetics of human ALCAM expression showed that its expression by mitogen activated peripheral blood T cells peaks 72 hours after stimulation and returns to undetectable levels between 5 and 8 hours. BEN/SC-1/DM-GRASP of the chicken is also expressed by activated T cells (Corbel et al., *Cell Immunol.* 141:99 (1992)) and hemopoietic progenitor cells and has been shown to mediate heterophilic interactions with NgCAM and other proteins (DeBernardo et al., *J. Cell. Biol.*, 133:657 (1996)). (Corbel et al., *PNAS*, 93:2844 (1996)). Studies of the role of CD6/ALCAM interactions in T cell regulation have shown that this receptor-ligand pair is able to mediate the adhesion of CD6 expressing cells to thymic epithelial cells (Bowen et al., *J. Exp. Med.*, 181:2213 (1995)). This and other evidence suggests that CD6/ALCAM interactions are important for modulating T cell development and activation.

Although the above findings indicate that CD6/ALCAM interactions play an important role in regulating T cell development and activation, there remains a clear need in the art for further discovery and characterization of CD6, and human CD6 in particular, especially with regard to its interactions with ALCAM. More specifically, there is a need in the art for further characterization of hCD6 structural elements that mediate hCD6/ALCAM binding interactions, and for specific tools, such as hCD6 binding agents, that can modulate hCD6/ALCAM interactions. Such tools would be useful in various diagnostic uses, ex vivo treatments, and in vivo therapeutic methods, for example for diagnosing CD6-mediated responses linked to disease states in patients, for conducting ex vivo affinity removal of CD6+ cells from transplant materials, and for providing in vivo modulating agents, e.g., inhibitors or enhancers, of CD6-mediated T cell activation, to modulate inflammatory and autoimmune responses in patients. The present invention addresses these needs and provides additional advantages that will become apparent from the description which follows.

SUMMARY OF THE INVENTION

The invention provides antibodies and other binding agents that bind specifically to SRCR domains of human CD6 (hCD6). In preferred aspects of the invention, antibodies and other immunoglobulins, including native and artificially modified antibodies and antibody fragments, are provided that bind specifically to human CD6 SRCR domain 3 (CD6D3) or human CD6 stalk domain (CD6S) and inhibit activated leukocyte cell adhesion molecule (ALCAM) binding to CD6.

In more detailed aspects of the invention, anti-human CD6 binding agents are selected from exemplary, native monoclonal antibodies identified hereinbelow and included within one of eight CD6 binding subgroups designated as Group 1 (exemplified by mAb 5D4); Group 2 (exemplified by mAb 10A5); Group 3 (exemplified by mAb 16A3); Group 4 (exemplified by mAb 7H6); Group 5 (exemplified by mAb 15B12); Group 6 (exemplified by mAbs 7C7 and 13C3); Group 7 (exemplified by mAbs 5E8 and 8A7); or Group 8 (exemplified by mAbs 10D1 and 12A5). Alternatively, anti-human CD6 binding agents may be selected from modified immunoglobulins, for example humanized antibodies, site directed mutagenized antibodies, or chemically or recombinantly produced antibody fragments, that exhibit substantial amino acid sequence identity to corresponding native antibodies and retain substantially the same CD6 binding specificity as the corresponding native antibody.

In other embodiments of the invention, screening methods are provided for identifying additional binding agents that specifically bind hCD6. These methods entail contacting a reference anti-hCD6 monoclonal antibody that binds specifically to human CD6 SRCR domain 3 (CD6D3) or human CD6 stalk domain (CD6S) and inhibits ALCAM binding to hCD6 with a target species comprising one or more hCD6 domains selected from CD6D2, CD6D3 and CD6S in the presence of a putative competitor test binding agent. This step of contacting is conducted under conditions suitable for complex formation between the reference antibody and the target species in the absence of the test binding agent. Next, complex formation between the reference antibody and the target species in the presence of the test binding agent is detected as an indicator of specific binding activity of the test binding agent to CD6D3 or CD6S. This screening method is useful for high throughput screening of, e.g., peptide and small molecule libraries to identify and characterize additional hCD6 binding agents. Preferred antibodies for these assays are also selected from the CD6 binding subgroups Group 1 (5D4); Group 2 (10A5); Group 3 (16A3); Group 4 (7H6); Group 5 (15B12); Group 6 (7C7, 13C3); Group 7 (5E8, 8A7); or Group 8 (10D1, 12A5), or from fragments or other artificially modified forms of these antibodies.

In related aspects of the invention, the foregoing screening methods are adapted by the additional steps of contacting ALCAM with the target species in the presence of the test binding agent under conditions suitable for ALCAM binding to the target species. Subsequently, complex formation is detected between ALCAM and the target species as an indicator of activity of the test binding agent for modulating ALCAM/CD6 binding. Preferred test binding agents for selection by such screening methods include peptide mimetics of a complementarity determining region (CDR) of the reference antibody, as well as other peptides and small molecular species that may be selected for their ability to modulate CD6/ALCAM binding interactions.

In other aspects of the invention, methods are provided for modulating inflammatory or autoimmune responses in patients, for example methods for inhibiting adverse responses associated with multiple sclerosis or transplant rejection. These methods include administration to a patient of a therapeutically or pharmaceutically effective amount of an anti-CD6 binding agent that binds specifically to human CD6 SRCR domain 3 (CD6D3) or human CD6 stalk domain (CD6S) and inhibits ALCAM binding to hCD6. Preferred anti-CD6 binding agents for use in these methods are monoclonal antibodies, including humanized monoclonal antibodies, as well as modified immunoglobulins such as antibody fragments and mutagenized forms of native antibodies having substantial amino acid sequence identity with a corresponding native antibody, and sharing substantially the same binding specificity therewith.

In yet additional aspects of the invention, diagnostic compositions and methods are provided for detecting CD6, CD6+ cells, and/or CD6-mediated activity, for example CD6 activity related to T cell activation, in in vitro and in vivo assays. These methods likewise employ anti-CD6 binding agents that bind specifically to human CD6 SRCR domain 3 (CD6D3) or human CD6 stalk domain (CD6S) and/or inhibit ALCAM binding to hCD6.

DESCRIPTION OF THE SPECIFIC EMBODIMENTS

I) Binding Agents

Figure 1:
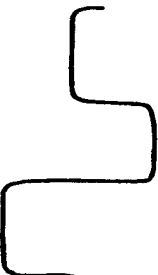
FIG. 1 schematically depicts CD6 and the various SRCR domains incorporated in different CD6-Rg fusion proteins used to characterize binding agents within the invention.
Figure 1:
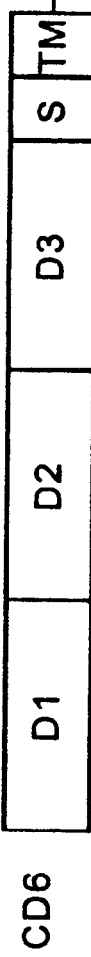
Figure 1:
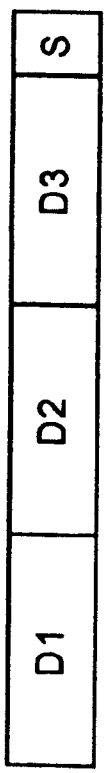
Figure 1:
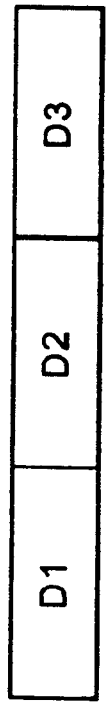
Figure 1:
Figure 1:
Figure 1:
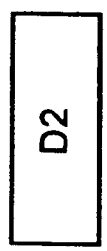
Figure 1:
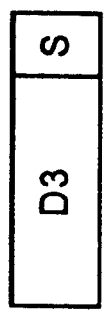

The invention provides antibodies, antibody fragments, and other binding agents that bind to one or more of the second SRCR domain (CD6D2), third (membrane proximal) SRCR domain (CD6D3) and stalk domain (CD6S) of human CD6, or that bind to a CD6 ligand, such as ALCAM. Preferred binding agents of the invention include native and modified antibodies and fragments thereof that bind specifically to one or more of the CD6D2, CD6D3 and CD6S domains. For these and other binding agents, specific binding exists when a dissociation constant for binding of the agent to CD6D2, CD6D3 or CD6D3S is $\leq 1\,\mu M$, preferably $\leq 100$ nM and most preferably $\leq 1$ nM. The ability of antibody to bind specifically to CD6D2, CD6D3 or CD6S can be determined based on affinity alone, or, alternatively or supplementally, using any of a wide variety of antibody specificity assays known in the art. Representative examples of such assays include: Countercurrent Immuno-Electrophoresis (CIEP), Radioimmunoassays, Enzyme-Linked Immunosorbent Assays (ELISA), Dot Blot assays, and Inhibition or Competition assays. These and other methods for determining antibody specificity and/or binding affinity are reviewed in *Antibodies: A Laboratory Manual*, Harlow and Lane (eds.), Cold Spring Harbor Laboratory Press, 1988, incorporated herein by reference in its entirety.

Antibodies useful within the present invention include native polyclonal and monoclonal antibodies, as well as genetically engineered and otherwise modified antibodies that retain substantially the same CD6D2, CD6D3 and CD6S domain binding specificity as a corresponding native antibody. Also provided are antibody fragments, including F(ab')$_2$ and F(ab') fragments, Fv fragments and unassociated heavy or light chains, and single-chain antibodies that specifically bind to CD6D2, CD6D3 or CD6S. As used herein, "native antibodies" and "native antibody fragments" means antibodies produced by conventional procedures of immunization and purification, as well as antibody fragments derived from intact native antibodies, e.g., by chemical or enzymatic separation.

For production of native antibodies, a CD6 protein, protein fragment or fusion protein comprising one or more CD6 domains, preferably in a substantially pure or isolated form, is administered to an animal such as a mouse, rat, horse, rabbit, goat or pig in an amount sufficient to cause an immune response in the animal. Preferably, the CD6 protein, protein fragment or fusion protein is administered in a mixture containing an adjuvant, such as Freund's adjuvant, in order to enhance the immune response. Although a single injection of antigen may be sufficient to induce antibody production in the animal, it is generally preferred to administer a large initial injection followed by one or more booster injections over a period of several weeks to several months. Blood is then collected from the animal and clotted, and antibodies are isolated from the serum using conventional techniques such as salt precipitation, ion exchange chromatography, affinity chromatography or high performance liquid chromatography.

In preferred embodiments of the invention, monoclonal antibodies are used. Monoclonal antibodies provide the advantages of ease of production and lower therapeutic doses as compared to polyclonal antisera, since only antibodies of the desired specificity are used. Methods for producing monoclonal antibodies are well known in the art and are disclosed, for example, by Kohler and Milstein, *Nature* 256:495 (1975); *Eur. J. Immunol.* 6:511–519 (1976); and Hurrell, J. G. R., ed., *Monoclonal Hybridoma Antibodies: Techniques and Applications*, CRC Press Inc., Boca Raton, Fla. (1982), each incorporated herein by reference in its entirety.

Preferably, the antibodies, antibody fragments, and other binding agents of the invention are provided in substantially pure, or isolated, form. As used herein, the terms "substantially pure" and "isolated" mean that an object species is the predominant species present (i.e., on a molar basis it is more abundant than any other individual species) in a composition. Preferably, the object species comprises at least about 50 percent (on a molar basis) of all macromolecular species present. More preferably, the object species in a substantially pure or isolated form will comprise more than about 80 to 90 percent of all macromolecular species present in a composition. Most preferably, the object species is purified to essential homogeneity (contaminant species cannot be detected in the composition by conventional detection methods) wherein the composition consists essentially of a single macromolecular species.

The antibodies, antibody fragments, and other binding agents of the invention preferably specifically inhibit binding of ALCAM to hCD6. By specifically inhibiting ALCAM binding to CD6 is meant that the binding agent blocks or competes with ALCAM binding in one or more competitive binding assays, such that ALCAM binding in the presence of the binding agent is inhibited by at least 10%, preferably by at least 25%, more preferably by at least 50%, and most preferably by at least 75%–90% or greater compared to ALCAM binding in a control assay in the absence of binding agent. The capacity to block or compete with ALCAM binding to CD6 may be determined by a variety of methods, as disclosed, for example in Bowen et al., *J. Biol. Chem.* 271:17390–17396, 1996, and as described in the Examples below.

The capacity to block, or compete with, ALCAM binding to CD6 typically indicates that an antibody, antibody fragment or other binding agent binds to a CD6 epitope or binding site that structurally overlaps with an ALCAM binding site of CD6, or to an epitope or binding site which is sufficiently proximal to an ALCAM binding site of CD6 to sterically or otherwise inhibit binding of ALCAM to CD6. Exemplary binding agents in this context include the ALCAM blocking, anti-human CD6D3 and anti-human CD6D3-S antibodies described herein and having CD6 binding characteristics of one of the CD6 binding subgroups designated hereinbelow as Group 1 (exemplified by mAb 5D4); Group 2 (exemplified by mAb 10A5); Group 3 (exemplified by mAb 16A3); Group 4 (exemplified by mAb 7H6); Group 5 (exemplified by mAb 15B12); Group 6 (exemplified by mAbs 7C7 and 13C3); Group 7 (exemplified by mAbs 5E8 and 8A7); and Group 8 (exemplified by mAbs 10D1 and 12A5). Hybridomas that express exemplary mAbs for each of these distinct CD6 binding subgroups have been deposited with the American Type Culture Collection (ATCC). Specifically, on Feb. 19, 1997, the following hybridomas were deposited with the American Type Culture Collection at 10801 University Boulevard, Manassas, Va. 20110-2209, and assigned the indicated deposit designation: (H6-2.7C7/designation HB12288); (H6-2.10A5/designation HB12289); (H6-2.10D1/designation HB12290); (H6-2.5D4/designation HB12291); (H6-1.7H6/designation HB12292); (H6-2.15B12/designation HB12293); (H6-2.14H2/designation HB12294); (H6-2.5E8/designation HB12295); and (H6-2.16A3/designation HB12296).

Additional binding agents provided within the invention include, for example, antibody fragments and recombinantly modified antibodies that share substantially similar CD6 domain specificity and binding affinity as a native anti-human CD6 antibody of the invention. Yet additional binding agents provided within the invention include, for example, mimetics of complementarity determining regions (CDRs) of the aforementioned anti-human CD6 antibodies, which mimetics are also capable of inhibiting ALCAM binding to CD6. Alternatively, binding agents of the invention may interfere with ALCAM\CD6 interactions by binding directly to human ALCAM at or sufficiently proximal to the CD6 binding domain of hALCAM (i.e., within or adjacent to the predicted A'GFCC'C" face of hALCAM, see, e.g., Bajorath et al., *Protein Science* 4:1644–1647, 1995; Skonier et al., *Biochemistry* 35:12287–12291, 1996; and Skonier et al., *Biochemistry* 35:14743–14748, 1996, each incorporated herein by reference in its entirety). Examples of this latter type of binding agent include peptide mimetics of CD6 epitopes recognized by reference anti-human CD6D3 or anti-human CD6S antibodies of the invention, wherein such epitopes share substantial sequence identity with an ALCAM binding site of CD6. Certain of these mimetics will also be recognized by ALCAM, whereby the mimetic will exhibit competitive inhibition against CD6 for ALCAM binding. Such mimetics can be routinely screened, for example, from commercially available peptide libraries based on well known assays to detect CD6 binding competition between a test mimetic and the anti-human CD6 reference antibody, whereafter test mimetics can be routinely selected based on ability to inhibit ALCAM binding to CD6, and/or modulate ALCAM binding inhibition by the reference antibody.

Antibodies, antibody fragments and other binding agents of the invention are provided that specifically inhibit CD6 binding by one or more selected anti-CD6D2, anti-CD6D3 or anti-CD6S reference antibodies disclosed herein (for example one or more reference antibodies selected from the binding groups designated Group 1 (5D4); Group 2 (10A5); Group 3 (16A3); Group 4 (7H6); Group 5 (15B12); Group 6 (7C7, 13C3); Group 7 (5E8, 8A7); and Group 8 (10D1, 12A5)) for binding to one or more CD6 domains. Competition is determined by an assay in which an antibody, antibody fragment, or other binding agent under test substantially inhibits specific binding of the reference antibody to a target species containing one or more CD6 domains, as determined for example by measuring binding of the reference antibody to a target species comprising CD6 or a CD6-Rg fusion protein including one or more of the CD6D2, CD6D3 and CD6S domains in the presence and absence of a putative competitor "test antibody" or other "test binding agent" under conditions suitable for complex formation between the reference antibody and the CD6 domain. Numerous types of competitive binding assays are known and routinely practicable within the invention, as described for example in U.S. Pat. Nos. 4,376,110 and 4,016,043, and Harlow and Lane, supra. Typically, such assays involve the use of a target species containing the CD6 domain(s) (e.g., purified CD6 or a purified Rg fusion protein including CD6D2, CD6D3 and/or CD6S), an unlabeled test antibody or other test binding agent, and a labeled reference antibody. The target species may be provided in the form of a biological sample (e.g. a sample of CD6+ cells), or may be provided as an artificial mixture such as a mixture containing a CD6-Rg fusion protein in solution or bound to a solid support, etc.

Competitive inhibition is measured by determining the amount of label bound to the target species in the presence of the test antibody or other test binding agent. Usually the test antibody or binding agent is present in excess. Antibodies and other binding agents identified by these competition assays ("competitive binding agents") include antibodies, antibody fragments and other binding agents that bind to an epitope or binding site bound by the reference antibody, as well as antibodies and other binding agents that bind to an epitope or binding site sufficiently proximal to an epitope bound by the reference antibody for competitive binding between the test binding agent and the reference antibody to occur. Competitive binding agents that compete with anti-human CD6 antibodies of the invention also include, e.g., peptide mimetics of CD6 epitopes bound by the reference antibody, which mimetics preferably bind to ALCAM in a competitive ALCAM/CD6 binding assay. Yet additional competitive binding agents include peptide mimetics of a complementarity determining region (CDR) of the reference antibody, which mimetics also preferably inhibit ALCAM/CD6 binding. Preferably, competitive binding agents of the invention will, when present in excess, inhibit specific binding of a reference antibody to a selected target species by at least 10%, preferably by at least 25%, more preferably by at least 50%, and most preferably by at least 75%–90% or greater.

II) Recombinant Production of Native and Modified Anti-CD6 Immunoglobulins and Antibody Fragments Antibodies, or immunoglobulins, are typically composed of four covalently bound peptide chains. For example, an IgG antibody has two light chains and two heavy chains. Each light chain is covalently bound to a heavy chain. In turn each heavy chain is covalently linked to the other to form a "Y" configuration, also known as an immunoglobulin conformation. Fragments of these molecules, or even heavy or light chains alone, may bind CD6. Antibodies, fragments of antibodies, and individual chains are also referred to herein as immunoglobulins.

Using well known methods of recombinant DNA technology, the immunoglobulins of the invention may be produced at high levels. In addition, native antibodies and antibody fragments can be routinely modified to yield modified anti-CD6 immunoglobulins having substantially similar or enhanced binding specificities and ALCAM blocking, or competition, activities as their corresponding parent anti-CD6 immunoglobulins. For example, genes encoding a native antibody (e.g., a gene encoding a Group 1 (5D4); Group 2 (10A5); Group 3 (16A3); Group 4 (7H6); Group 5 (15B12); Group 6 (7C7, 13C3); Group 7 (5E8, 8A7); or Group 8 (10D1, 12A5) monoclonal antibody as described herein) can be isolated and cloned into one or more polynucleotide expression vectors, and the vector can be transformed into a suitable host cell line for expression of a recombinant antibody. Expression of the cloned antibody encoding gene provides for increased yield of antibody, and also allows for routine modification of native immunoglobulins by introducing amino acid substitutions, deletions, additions and other modifications, for example humanizing modifications, in both the variable and constant regions without critical loss of binding specificity or ALCAM blocking function.

Genes encoding the heavy and light chains of anti-CD6 immunoglobulins are isolated and cloned according to methods, known in the art, for example according to methods described in Sambrook et al., *Molecular Cloning: A Laboratory Manual,* (2nd ed., Cold Spring Harbor, N.Y., 1989; Berger & Kimmel, *Methods in Enzymology, Volume 152, Guide to Molecular Cloning Techniques,* (Academic Press, Inc., San Diego, Calif., 1987); Co et al., *J. Immunol.,* 148:1149 (1992), each of which is incorporated herein by reference for all purposes. In certain aspects of the invention genes encoding heavy and light chains are cloned from genomic DNA of a selected, anti-human CD6 producing hybridoma, or, alternatively, from cDNA produced by reverse transcription of the hybridoma's RNA. Cloning is accomplished by conventional techniques, including for example the use of PCR primers that hybridize to the sequences flanking or overlapping the genes, or segments of genes, to be cloned.

Recombinant constructs according to the invention may comprise DNA segments encoding a complete, native anti-human CD6 immunoglobulin heavy chain and/or a complete, native anti-human CD6 immunoglobulin light chain of an immunoglobulin expressed by a hybridoma cell line. Alternatively, DNA segments encoding only one or more fragments of a native anti-human CD6 antibody are produced, which one or more fragments possess substantially similar or enhanced binding and/or effector activities as the native immunoglobulin. Other recombinant constructs contain segments of hybridoma cell line immunoglobulin genes encoding fragments of a native anti-human CD6 antibody fused to segments of other immunoglobulin genes, particularly segments of human constant region sequences (heavy and/or light chain). Human constant region sequences can be selected from various reference sources, including but not limited to those listed in Kabat et al., supra.

In addition to the DNA segments encoding native anti-human CD6 immunoglobulins or fragments thereof, modified immunoglobulins or antibody fragments having substantially similar or enhanced binding specificities and blocking activities as their corresponding parent anti-CD6 immunoglobulins can be readily designed and manufactured utilizing various recombinant DNA techniques known to those skilled in the art, such as site-directed mutagenesis. Such modified immunoglobulins, including antibody fragments, will preferably retain substantially the same antigen binding specificity and/or effector function as a corresponding native anti-human CD6 immunoglobulin or antibody fragment, and may exhibit enhanced binding affinity compared to the corresponding native immunoglobulin or antibody fragment. Moreover, the polynucleotide sequences encoding modified immunoglobulins and antibody fragments are preferably substantially identical to the original hybridoma genomic or cDNA sequences so as to allow hybridization to these sequences under stringent conditions.

Recombinant polynucleotide constructs suitable for expression of the native and modified immunoglobulins and antibody fragments of the invention will typically include an expression control sequence, including naturally-associated or heterologous promoter regions, operably linked to one or more desired coding sequences. Preferably, the expression control sequences will be eukaryotic promoter systems in vectors capable of transforming or transfecting eukaryotic host cells. Once the vector has been incorporated into an appropriate host cell, the host cell is maintained under conditions suitable for expression of the coding sequences, and for subsequent collection and purification of the native or modified anti-human CD6 immunoglobulin or antibody fragment.

Expression vectors suitable for use within the invention are typically replicable in host cells either as episomes or as an integral part of the host chromosomal DNA. Commonly, expression vectors will contain selection markers, e.g., ampicillin-resistance or hygromycin-resistance, to permit detection of cells transformed with the desired DNA sequences.

In general, prokaryotes can be used for cloning the DNA sequences encoding a native or modified anti-human CD6 immunoglobulin or antibody fragment. *E. coli* represents one prokaryotic host that is particularly useful for cloning the DNA sequences of the present invention. Other hosts, such as yeast, are also useful for cloning and expression purposes. Saccharomyces is a preferred yeast host, with suitable vectors having expression control sequences, an origin of replication, termination sequences and the like as desired. Typical promoters include 3-phosphoglycerate kinase and other glycolytic enzymes. Inducible yeast promoters include, among others, promoters from alcohol dehydrogenase 2, isocytochrome C, and enzymes responsible for maltose and galactose utilization.

Mammalian cells are particularly preferred as host cells for expressing nucleotide segments encoding immunoglobulins or fragments thereof. (See, e.g., Winnacker, *From Genes to Clones,* (VCH Publishers, NY, 1987, incorporated herein by reference in its entirety). A number of suitable host cell lines capable of secreting intact heterologous proteins have been developed in the art, and include CHO cell lines, various COS cell lines, HeLa cells, L cells and myeloma cell lines. Preferably, the cells are nonhuman. Expression vectors for these cells can include expression control sequences, such as an origin of replication, a promoter, an enhancer (See, e.g., Queen et al., *Immunol. Rev.* 89:49 (1986), incorporated herein by reference in its entirety), and necessary processing information sites, such as ribosome binding sites, RNA splice sites, polyadenylation sites, and transcriptional terminator sequences. Preferred expression control sequences are promoters derived from endogenous genes, cytomegalovirus, SV40, adenovirus, bovine papillomavirus, and the like. (See, e.g., Co et al., *J. Immunol.* 148:1149 (1992), incorporated herein by reference in its entirety).

Vectors containing immunoglobulin encoding DNA segments of interest can be transferred into the host cell by well-known methods, depending on the type of host cell. For example, calcium chloride transfection is commonly utilized for prokaryotic cells, whereas calcium phosphate treatment, electroporation, lipofection, biolistics or viral-based transfection may be used for other cellular hosts. Other methods used to transform mammalian cells include the use of polybrene, protoplast fusion, liposomes, electroporation, and microinjection (see, e.g., Sambrook et al., supra).

Once expressed, anti-human CD6 immunoglobulins and antibody fragments of the invention can be purified according to standard methods in the art, including HPLC purification, fraction column chromatography, gel electrophoresis and the like (see, e.g., Scopes, *Protein Purification,* Springer-Verlag, NY, 1982, incorporated herein by reference in its entirety).

Many of the native anti-human CD6 immunoglobulins and antibody fragments described herein can undergo non-critical amino acid substitutions, additions, deletions and other modifications in both the variable and constant regions without loss of binding specificity or ALCAM blocking function (e.g. without reduction of CD6 binding affinity to below about $10^7$ $M^{-1}$). Usually, immunoglobulins and antibody fragments incorporating such modifications exhibit substantial sequence identity to native immunoglobulins or antibody fragments from which they were derived. Preferably, mature light chains of antibodies derived from native antibodies of the invention (e.g., Group 1 (5D4); Group 2 (10A5); Group 3 (16A3); Group 4 (7H6); Group 5 (15B12); Group 6 (7C7, 13C3); Group 7 (5E8, 8A7); or Group 8 (10D1, 12A5)) exhibit substantial amino acid sequence identity to the amino acid sequence of a mature light chain of the corresponding native antibody. Similarly, the mature heavy chains of modified anti-CD6 immunoglobulins of the invention typically exhibit substantial sequence identity to the sequence of the mature heavy chain of the corresponding native antibody. As applied to polypeptides, the term "substantial sequence identity" means that two polypeptide sequences, when optimally aligned, such as by the programs BLAZE (Intelligenetics) GAP or BESTFIT using default gap weights, share at least 70 percent or 85 percent sequence identity, preferably at least 90 percent sequence identity, more preferably at least 95 percent sequence identity or more (e.g., 99 percent sequence identity). Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

Occasionally, a modified anti-CD6 immunoglobulin of the invention can be selected having increased affinity compared with that of a native anti-CD6 immunoglobulin from which it was derived. More typically, the affinity of a modified anti-CD6 immunoglobulin will be within a range of 20–50 fold greater or lesser than, or substantially the same as (i.e. within a factor of 2–5 greater or lesser than) the affinity of the corresponding native immunoglobulin, as determined for example by comparative binding of the modified and native immunoglobulins to a target species containing relevant CD6 domain(s) (e.g., purified CD6 or a purified CD6-Rg fusion protein including CD6D2, CD6D3 and/or CD6S). Phage-display technology offers one of a number of powerful techniques well known in the art that are useful for selecting such immunoglobulins. (See, e.g., Dower et al., WO 91/17271; McCafferty et al., WO 92/01047; and Huse, WO 92/06204, each of which is incorporated by reference in its entirety for all purposes).

Polynucleotides encoding modified anti-CD6 immunoglobulins of the invention are also selected based on a desired sequence relationship to a polynucleotide "reference sequence" encoding a native anti-CD6 antibody or antibody fragment. As used herein, a polynucleotide "reference sequence" is a defined sequence used as a basis for a sequence comparison; a reference sequence may be a subset of a larger sequence, for example, as a segment of a full-length cDNA or gene sequence encoding a native anti-CD6 mAb or antibody fragment. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Natl. Acad. Sci.* (USA) 85:2444 (1988) (each of which is incorporated by reference in its entirety), by computerized implementations of these algorithms (GAP, BESTFIT, FASTA, and TFASTA in the Wisconsin Genetics Software Package Release 7.0, Genetics Computer Group, 575 Science Dr., Madison, Wis., incorporated herein by reference), or by inspection, and the best alignment (i.e., resulting in the highest percentage of sequence similarity over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity.

For the purposes of the present invention, mutant polynucleotides encoding modified anti-CD6 immunoglobulins exhibit substantial sequence identity to a polynucleotide reference sequence encoding a native anti-CD6 antibody or antibody fragment. As used herein and applied to polynucleotides, "substantial identity" denotes that a mutant polynucleotide encoding a modified anti-CD6 immunoglobulin exhibits at least 85 percent sequence identity, preferably at least 90 to 95 percent sequence identity, more usually at least 99 percent sequence identity as compared to a reference sequence (e.g., a genomic or cDNA polynucleotide encoding Group 1 (5D4); Group 2 (10A5); Group 3 (16A3); Group 4 (7H6); Group 5 (15B12); Group 6 (7C7, 13C3); Group 7 (5E8, 8A7); or Group 8 (10D1, 12A5)) over a comparison window of at least 20 nucleotide positions, frequently over a comparison window of at least 25–50 nucleotides, wherein the percentage of sequence identity is calculated by comparing the reference sequence to the mutant polynucleotide sequence which may include deletions or additions which total 20 percent or less of the reference sequence over the window of comparison.

A) Humanized Antibodies

For diagnostic and therapeutic purposes, it is generally preferred to use anti CD6 antibodies or antibody fragments that are syngeneic with a patient, e.g. a human patient, or that contain syngeneic constant regions. For this reason, genetically engineered antibodies will generally be used in the treatment of humans. Methods for producing recombinant human antibodies or humanized non-human (i.e., chimeric) antibodies are disclosed, for example, by Cabilly et al. (U.S. Pat. No. 4,816,567); Robinson et al. (WO 87/02671); and Neumaier (WO 90/00616), each of which is incorporated herein by reference in its entirety. Briefly, human constant region genes are joined to appropriate human or non-human variable region genes. For example, the amino acid sequences which represent the antigen binding sites (CDRs, or complimentarity-determining regions) of a parent murine monoclonal antibody are grafted at the DNA level onto human variable region framework sequences. This process is known as "humanization". Methods for this technique are known in the art and are disclosed, for example, by Jones et al., *Nature*, 326:522–525, (1986)); Riechmann et al., *Nature*, 322:323–327 (1988)); and Queen et al., *Proc. Natl. Acad. Sci. USA* 86:10029–10033 (1989), each of which is incorporated herein by reference in its entirety.

Immunoglobulin encoding polynucleotides thus chimerized are then transfected into host cells, which are cultured to express a humanized immunoglobulin according to conventional procedures. In the alternative, monoclonal antibody producing cells may be transfected with cloned human constant region genes, and chimeric antibody genes generated by homologous recombination. Thus it is possible to assemble monoclonal antibodies with a significant portion of the structure being human, thereby providing antibodies that are more suitable for multiple administrations to human patients. Alternatively, a single chain antibody may be developed through the expression of a recombinant polypeptide which is generally composed of a variable light-chain sequence joined, typically via a linker polypeptide, to a variable heavy-chain sequence. Methods for producing single chain antibodies are known in the art and are disclosed, for example, by Davis et al. (*BioTechnology* 9: 165–169, 1991, incorporated herein by reference in its entirety).

Preferred methods for producing humanized antibodies of the invention involve substitution of mouse CDRs into a human variable domain framework. This technique is most likely to result in retention of a correct spatial orientation for the resulting immunoglobulin if the human variable domain framework adopts the same or similar conformation to the mouse variable framework from which the CDRs originated. This is achieved by obtaining the human variable domains from human antibodies whose framework sequences exhibit a high degree of sequence identity with the murine variable framework domains from which the CDRs were derived. The heavy and light chain variable framework regions can be derived from the same or different human antibody sequences. The human antibody sequences can be the sequences of naturally occurring human antibodies or can be consensus sequences of several human antibodies. (See, e.g., Kettleborough et al., *Protein Engineering*, 4:773 (1991); and Kolbinger et al., *Protein Engineering*, 6:971 (1993), each incorporated herein by reference in its entirety).

Identification of suitable human antibody sequences may be facilitated by computer comparisons of the amino acid sequences of, e.g., mouse variable regions with corresponding sequences of known human antibodies. Such comparisons are well known in the art, and are used, for example, to avoid unnatural juxtaposition of non-human CDR regions with human variable framework regions, which can result in unnatural conformational restraints and concomitant loss of binding affinity. Computer hardware and software for producing three-dimensional images of immunoglobulin molecules are widely available. In general, molecular models are produced starting from solved structures for immunoglobulin chains or domains thereof. The chains to be modelled are compared for amino acid sequence similarity with chains or domains of solved three dimensional structures, and the chains or domains showing the greatest sequence similarity is/are selected as starting points for construction of the molecular model. The solved starting structures are modified to allow for differences between the actual amino acids in the immunoglobulin chains or domains being modelled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits. Additional models can be constructed representing the structure when further amino acid substitutions to be discussed infra, are introduced.

As noted above, the humanized antibodies of the invention comprise variable framework regions from a human immunoglobulin and complementarity determining regions from a mouse immunoglobulin. Having identified the complementarity determining regions of a selected anti-CD6 immunoglobulin, and appropriate human acceptor immunoglobulins, the next step is to determine which, if any, residues from these components should be substituted to optimize the properties of the resulting humanized antibody. In general, substitution of human amino acid residues with murine should be minimized, because introduction of murine residues increases the risk of the antibody eliciting a HAMA response in humans. Amino acids are selected for substitution based on their possible influence on CDR conformation and/or binding to antigen. Investigation of such possible influences is by modelling, examination of the characteristics of the amino acids at particular locations, or empirical observation of the effects of substitution or mutagenesis of particular amino acids.

When an amino acid differs between an anti-human CD6 immunoglobulin variable framework region and an equivalent human variable framework region, the human framework amino acid should usually be substituted by the equivalent mouse amino acid if it is reasonably expected that the amino acid:

(1) noncovalently binds antigen directly;
(2) is adjacent to a CDR region, is part of a CDR region under the alternative definition proposed by Chothia et al., supra, or otherwise interacts with a CDR region (e.g., is within about 3 Å of a CDR region); and/or
(3) participates in the $V_L$-$V_H$ interface;

Other candidates for substitution are acceptor human framework amino acids that are atypical for human immunoglobulins at that position. These amino acids can be substituted with amino acids from the equivalent position of more typical human immunoglobulins. Alternatively, amino acids from equivalent positions in the mouse immunoglobulin can be introduced into the human framework regions when such amino acids are typical of human immunoglobulin at the equivalent positions.

In general, substitution of all or most of the amino acids fulfilling the above criteria is desirable. Occasionally, however, there is some ambiguity about whether a particular amino acid meets the above criteria, in which case alternative variant immunoglobulins may be produced and tested for desired binding specificity (one of which has that particular substitution, the other of which does not).

Usually the CDR regions in humanized antibodies are substantially identical, and, more usually, identical to the corresponding CDR regions in a corresponding, native murine anti-human CD6 antibody. Occasionally, however, it is desirable to substitute one or more of the residues in a CDR region. For example, residues that differ at corresponding positions within CDR regions of two mAbs within an exemplary binding group (e.g., Group 1 exemplified by mAb 5D4; Group 2 exemplified by mAb 10A5; Group 3 exemplified by mAb 16A3; Group 4 exemplified by mAb 7H6; Group 5 exemplified by mAb 15B12; Group 6 exemplified by mAbs 7C7 and 13C3; Group 7 exemplified by mAbs 5E8 and 8A7; and Group 8 exemplified by mAbs 10D1 and 12A5) may be substituted one for the other with little or no loss of binding specificity, particularly if a conservative substitution is involved. Alternatively, CDR residues from mAbs that exhibit very high binding affinities and/or inhibit ALCAM binding very effectively may be substituted within a CDR region of other anti-human CD6 antibody with the potential result of conferring higher affinity binding to the substituted antibody. Although not usually desirable, it is sometimes possible to make more than one conservative amino acid substitutions of CDR residues without appreciably affecting the binding affinity of the resulting humanized immunoglobulin.

Other than for the specific amino acid substitutions discussed above, the framework regions of humanized immunoglobulins are usually substantially identical, and more usually, identical to the framework regions of the human antibodies from which they were derived. Of course, many of the amino acids in the framework region make little or no direct contribution to the specificity or affinity of an antibody. Thus, many individual conservative substitutions of framework residues can be tolerated without appreciable change of the specificity or affinity of the resulting humanized immunoglobulin. However, in general, such substitutions are undesirable.

Having conceptually selected the CDR and framework components of humanized immunoglobulins, a variety of methods are available for producing such immunoglobulins. Because of the degeneracy of the code, a variety of nucleic acid sequences will encode each immunoglobulin amino acid sequence. The desired nucleic acid sequences can be produced by de novo solid-phase DNA synthesis or by PCR mutagenesis of an earlier prepared variant of the desired polynucleotide. Oligonucleotide-mediated mutagenesis is a preferred method for preparing substitution, deletion and insertion mutants of polynucleotides encoding immunoglobulins of the invention. (See, e.g., Adelman et al., *DNA*, 2:183 (1983), incorporated herein by reference in its entirety). Briefly, the target immunoglobulin encoding polynucleotide is altered by hybridizing an oligonucleotide encoding the desired mutation to a single-stranded DNA template. After hybridization, a DNA polymerase is used to synthesize an entire second complementary strand of the template that incorporates the oligonucleotide primer, and encodes the selected alteration in the target immunoglobulin encoding polynucleotide.

The variable segments of humanized antibodies produced as described supra are typically linked to at least a portion of an immunoglobulin constant region (Fc), typically that of a human immunoglobulin. Human constant region DNA sequences can be isolated in accordance with well-known procedures from a variety of human cells, but preferably immortalized B-cells. (See, e.g., Kabat et al., supra; and WO87/02671, each of which is incorporated by reference in its entirety for all purposes). Ordinarily, the antibody will contain both light chain and heavy chain constant regions. The heavy chain constant region usually includes CH1, hinge, CH2, CH3, and CH4 regions.

B) Bifunctional Antibodies and Antibody Panels

Monoclonal antibodies can also be used to develop bifunctional antibodies where there are two independent antigenic binding moieties on each immunoglobulin molecule according to well known methods. Additionally, bispecific antibodies can also be constructed from single chain antibodies. This technology is also known in the art, as described, for example, by A. George, in *The Second Annual IBC International Conference on Antibody Engineering*, Dec. 16–18, 1991, San Diego Calif.

The anti-human CD6 antibodies and antibody fragments used within the methods of the invention may also be desirably combined to form a panel of antibodies or antibody fragments capable of inhibiting ALCAM binding to CD6. As used herein, the term "panel" denotes a combination of two or more antibodies or antibody fragments having different domain or epitope specificities (e.g., that bind to separate CD6 domains, or to separate epitopes within a single CD6 domain).

II) Diagnostic and Therapeutic Uses of Anti-Human CD6 Immunoglobulins and Antibody Fragments A) Diagnostics Anti-human CD6 antibodies, antibody fragments and other binding agents of the invention may be used as targeting or imaging agents for the delivery of compounds and labeling moieties of therapeutic or diagnostic interest. Like many other genes, immunoglobulin genes contain separate functional regions, each having one or more distinct biological activities. Accordingly, the immunoglobulin genes of the invention may be fused to functional regions from other genes according to well known methods to produce fusion proteins (e.g., immunotoxins) having novel properties or novel combinations of properties. Such compounds include, but are not limited to, toxins, cytostatic compounds, or proenzymes whose potential function can be to activate endogenous proenzymes, to activate proenzymes added from exogenous sources, or to activate enzyme cleavage sites on prodrugs. Anti-human CD6 receptor antibodies and antibody fragments can further be employed as imaging agents, for example by labeling the antibody with radionucleotides, dyes, fluorescent compounds or the like. Examples of this use include imaging sites of inflammation where CD6 expression may be detected and/or quantified as an diagnostic or prognostic indicator of the nature and extent of inflammatory or autoimmune responses mediated by CD6.

The antibodies of the invention, their binding fragments and other binding agents disclosed herein are particularly useful for detecting the presence and/or activity of CD6 and CD6+ cells for diagnostic purposes. The presence of CD6+ cells in a diagnostic sample from a patient (e.g., a blood sample, or a tissue biopsy taken from a site of suspected inflammation or autoimmune activity) may be diagnostic of an aberrant inflammatory or autoimmune response and may signal the need for commencement of a therapeutic method, discussed infra. Diagnosis can be accomplished by removing a diagnostic sample from a patient and qualitatively or quantitatively assessing CD6+ expression or activity in the sample. For example, the number of CD6+ cells in a blood sample from a patient at risk for inflammatory or autoimmune disease can be compared to CD6+ cell levels in a control sample from a normal patient not at such risk (or to an established normal level of CD6+ cells without using an actual control sample). Similarly, CD6 expression by CD6+ cells, including both the pattern and level of expression, can be evaluated in diagnostic samples, e.g., by immunohistochemical staining of fixed cells or Western blotting of cell extracts using, e.g., humanized anti-CD6 antibodies of the invention or binding fragments thereof. In performing these methods the antibody or other binding agent may be directly labeled or, more typically in the case of antibodies, secondarily labeled, e.g., by an enzyme-conjugated secondary antibody directed against the desired antigen-monoclonal antibody complex.

Diagnosis can also be achieved by in vivo administration of anti-CD6 antibodies, antibody fragments, and other binding agents of the invention, followed for example by detection of these binding agents according to known methods of in vivo imaging. The concentration of binding agent administered should be sufficient that binding of the agent to cells expressing a target CD6 domain is detectable compared to background signal. The diagnostic reagent can be labeled, for example, with a radioisotope for camera imaging, or a paramagnetic isotope for magnetic resonance or electron spin resonance imaging.

A change (typically an increase) in the level of CD6+ cells or CD6 expression by such cells in a cellular sample, or imaged from an individual, which is outside a range of clinically established normal levels, may indicate the presence of an undesirable inflammatory or autoimmune response reaction in the individual from whom the sample was obtained, and/or indicate a predisposition of the individual for developing (or progressing through) such a reaction. Alternatively, diagnostic reagents including binding agents of the invention can be used as a differentiation marker to identify and type cells of certain lineages and developmental origins. Such cell-type specific detection can be used, for example, in histopathological diagnoses of undesired inflammatory or autoimmune responses.

B) Therapeutic Compositions and Treatment Methods

The invention also provides therapeutic compositions and methods of treatment that exploit the capacity of immunoglobulins and other binding agents of the invention to modulate ALCAM binding to CD6 and otherwise affect CD6 expression and activity to modulate inflammatory and autoimmune reactions in patients. As noted above, CD6 is an important regulator of early T cell development, activation and signal transduction. The activity and expression of CD6 is in turn mediated by its binding interaction with ALCAM. For example, the activity of CD6 in promoting T cell adhesion to TE cells is mediated by ALCAM binding to CD6, and pretreatment of CD6 transfected COS cells with an anti-ALCAM mAb inhibits this CD6 mediated adhesion. (See, e.g., Bowen et al., *J. Ex. Med.* 181: 2213–2220, 1995, incorporated herein by reference in its entirety). Accordingly, the anti-human CD6D3 and anti-human CD6D3-S antibodies, antibody fragments and other binding agents of the invention that inhibit ALCAM binding to CD6 via a novel mechanism will be employed to inhibit CD6 mediated T cell adhesive interactions with TE cells in vivo, to prevent or substantially reduce T cell mediated inflammatory and autoimmune responses in patients. Preferred binding agents in this context will be selected by pre-screening in in vitro assays, for example by adapting the CD6+ COS cell transfectant/TE cell adhesion assays described in Bowen et al., supra. Alternative selection of therapeutic binding agents may be routinely conducted by assaying activity of candidate binding agents for modulating CD6 hyperphosphorylation on Ser and Thr residues (Swack et al., *Mol. Immunol.* 26:1037–1049 (1989); Swack et al., *J. Biol. Chem.* 266:7137 (1991); Cardenas et al., *J. Immunol.*, 145:1450–1455 (1990), each incorporated herein by reference in its entirety) and/or CD6 phosphorylation on Tyr residues (Wee et al., *J. Exp. Med.,* 177:219–223 (1993)) associated with T cell activation in the presence and absence of a candidate, therapeutic binding agent.

Diseases and conditions resulting from inflammation and autoimmune disorders that may be subject to treatment using the compositions and methods of the invention include multiple sclerosis, meningitis, encephalitis, stroke, other cerebral traumas, inflammatory bowel disease including ulcerative colitis and Crohn's disease, rheumatoid arthritis, asthma, acute juvenile onset diabetes, AIDS dementia, atherosclerosis, nephritis, retinitis, atopic dermatitis, psoriasis, myocardial ischemia and acute leukocyte-mediated lung injury.

Still other indications for therapeutic use of antibodies and other binding agents of the invention include a risk of organ or graft rejection. Over recent years there has been a considerable improvement in the efficiency of surgical techniques for transplanting tissues and organs such as skin, kidney, liver, heart, lung, pancreas and bone marrow. Perhaps the principal outstanding problem is the lack of satisfactory agents for inducing immunotolerance in the recipient to the transplanted allograft or organ. When allogeneic cells or organs are transplanted into a host (i.e., the donor and donee are different individuals from the same species), the host immune system is likely to mount an immune response to foreign antigens in the transplant (host-versus-graft disease) leading to destruction of the transplanted tissue.

Antibodies and other binding agents that modulate CD6 expression or activity may be useful, inter alia, to block alloantigen-induced immune responses in a donee, thereby preventing or reducing CD6 mediated mechanisms that may contribute to the destruction of transplanted tissues or organs. See, e.g., Paul et al., *Transplant International,* 9:420–425 (1996); Georczynski et al., *Immunology,* 87:573–580 (1996); Georcyznski et al., *Transplant. Immunol.,* 3:55–61 (1995); Yang et al., *Transplantation,* 60:71–76 (1995); Anderson et al., *APMIS,* 102:23–27 (1994). In this context, anti-CD6 mAbs have been shown to act as immunosuppressive agents for patients undergoing renal or bone marrow allograft rejection (see, e.g. Kirkman et al., *Transplantation* 36:600 (1983); and Reinherz et al., *Proc. Natl. Acad. Sci. USA,* 79:6047 (1982) each incorporated herein by reference in its entirety.

A related use for antibodies and other binding agents of the invention that modulate CD6 expression or activity include modulation of immune responses involved in "graft versus host" disease (GVHD). See e.g., Schlegel et al., *J. Immunol.* 155:3856–3865 (1995). GVHD is a potentially fatal disease that occurs when immunologically competent cells are transferred to an allogeneic recipient. In this situation, the donor's immunocompetent cells may attack tissues in the recipient. Tissues of the skin, gut epithelia and liver are frequent targets and may be destroyed during the course of GVHD. The disease presents an especially severe problem when immune tissue is being transplanted, such as in bone marrow transplantation; but less severe GVHD has also been reported in other cases as well, including heart and liver transplants. The therapeutic agents of the present invention are used, inter alia, to block activation of the donor T cells, thereby interfering with their ability to lyse target cells in the host.

A particularly preferred use of the antibodies and other binding agents of the invention is for treating multiple sclerosis. Multiple sclerosis is a progressive neurological autoimmune disease that affects an estimated 250,000 to 350,000 people in the United States. Multiple sclerosis is thought to be a the result of a specific autoimmune reaction in which certain leukocytes attack and initiate the destruction of myelin, the insulating sheath covering nerve fibers. In animal models for multiple sclerosis, monoclonal antibodies that block the adhesion of leukocytes to endothelium have been shown to prevent inflammation of the central nervous system and subsequent paralysis in the animals. In addition, in vivo studies using mAbs against CD6, albeit unrelated to those of the invention, suggest that CD6 has important immunomodulatory effects in patients with multiple sclerosis. (See, e.g., Hafler et al., *Neurology* 36:777 (1986) incorporated herein by reference in its entirety).

For multiple sclerosis and other treatment indications, preferred binding agents of the invention are humanized mAbs and antibody fragments, as described above. These binding agents offer several advantages over the mouse antibodies already shown to be effective in animals models:

1) The human immune system should not recognize the framework or constant region of the humanized antibody as foreign, and therefore the antibody response against such an injected antibody should be less than against a totally foreign mouse antibody or a partially foreign chimeric antibody.

2) Because the effector portion of the humanized antibody is human, it may interact better with other parts of the human immune system.

3) Injected mouse antibodies have been reported to have a half-life in the human circulation much shorter than the half-life of normal human antibodies (Shaw et al., *J. Immunol.* 138:4534–4538 (1987)). Injected humanized antibodies have a half-life essentially equivalent to naturally occurring human antibodies, allowing smaller and less frequent doses.

The binding agents of the invention may be administered in pharmaceutical compositions for prophylactic and/or therapeutic treatments of the previously listed inflammatory and autoimmune disorders, including multiple sclerosis, inflammatory bowel disease, asthma, atherosclerosis, rheumatoid arthritis, organ or graft rejection and graft versus host disease. In therapeutic applications, compositions are administered to a patient suspected of, or already suffering from such a disease in an amount sufficient to cure, or at least partially arrest, the symptoms of the disease and its complications. An amount adequate to accomplish this is defined as a therapeutically- or pharmaceutically-effective dose.

In prophylactic applications, pharmaceutical compositions are administered to a patient susceptible to, or otherwise at risk of, a particular disease in an amount sufficient to eliminate or reduce the risk or delay the outset of the disease. Such an amount is defined to be a prophylactically effective dose. In patients with multiple sclerosis in remission, risk may be assessed by NMR imaging or, in some cases, by presymptomatic indications observed by the patient.

Pharmaceutical compositions incorporating binding agents of the invention used for prophylactic or therapeutic treatment are provided in a variety of forms. The preferred form depends on such routine variables as the intended mode of administration and therapeutic application. The compositions will generally include, depending on the formulation desired, pharmaceutically-acceptable, non-toxic carriers or diluents, which include a wide range of delivery vehicles commonly used to formulate pharmaceutical compositions for animal or human administration. Suitable carriers and diluents are selected so as not to significantly impair biological activity of the binding agent (e.g., binding specificity, affinity or stability). Examples of such diluents are distilled water, physiological saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

The pharmaceutical compositions will be administered by parenteral, topical, intravenous, oral, or subcutaneous, intramuscular local administration, such as by aerosol or transdermally, for prophylactic and/or therapeutic treatment. Although the proteinaceous substances of this invention may survive passage through the gut following oral administration, subcutaneous, intravenous, intramuscular, intraperitoneal administration by depot injection; or by implant preparation. are preferred.

The pharmaceutical compositions can be administered in a variety of unit dosage forms depending upon the method of administration. For example, unit dosage forms suitable for oral administration include powder, tablets, pills, capsules, and lozenges.

Effective doses of the compositions of the present invention for the treatment of the above described conditions will vary depending upon many different factors, including means of administration, target site, physiological state of the patient, and other medicants administered. Thus, treatment dosages will need to be titrated to optimize safety and efficacy. These compositions may be administered to mammals for veterinary use and for clinical use in humans in a manner similar to other therapeutic agents, i.e., in a physiologically acceptable carrier. In general, the administration dosage will range from about 0.0001 to 100 mg/kg, and more usually 0.01 to 5 mg/kg of the host body weight.

In a preferred treatment regime, the antibody is administered by intravenous infusion or subcutaneous injection at a dose from 1 to 5 mg antibody per kilo of bodyweight. The dose is repeated at interval from 2 to 8 weeks. Within this range, the preferred treatment regimen is 3 mg antibody per kilo of bodyweight repeated at a 4 week interval.

The humanized antibodies and other binding agents of the invention can be used with effective amounts of other therapeutic agents against acute and chronic inflammation. Such agents include antibodies and other antagonists of adhesion molecules, including integrins, selecting, and immunoglobulin (Ig) superfamily members. Other antiinflammatory agents that can be used in combination with the antibodies and other blocking agents of the invention include other antibody and non-antibody antagonists of cytokines, such as interleukins IL-1 through IL-13, tumor necrosis factors α & β, interferons α, β and γ, tumor growth factor Beta (TGF-β), colony stimulating factor (CSF) and granulocyte monocyte colony stimulating factor (GM-CSF). Likewise, antibodies and other antagonists of chemokines such as MCP-1, MIP-1α, MIP-1β, rantes, exotaxin and IL-8 are also useful in combination with the binding agents of the invention, as are antiinflammatory drugs such as NSAIDS, steroids and other small molecule inhibitors of inflammation.

C) Additional Uses

The antibodies and other binding agents of the invention are also useful for affinity purification of CD6. For example, the antibodies can be immobilized to a solid support and a solution of dispersed proteins including CD6 passed over the support to separate CD6 from other proteins in the solution. The purified CD6 or fragments thereof obtained by such methods can be used for a number of purposes, e.g., as a vaccine or as an immunogen for producing further anti CD6 antibodies.

The antibodies and antibody fragments of the invention are also useful for generating idiotypic antibodies by, for example, immunization of an animal with a humanized antibody. An anti-idiotype antibody whose binding to the human antibody is inhibited by CD6 or fragments thereof is selected. Because both the anti-idiotypic antibody and the CD6 or CD6 fragments bind to the humanized immunoglobulin, the anti-idiotypic antibody may represent an "internal image" of an epitope and thus may substitute a ligand of CD6.

In addition to their use as tools to study and modulate T cell activation, anti-CD6 antibodies and antibody fragments may be used in a clinical setting as affinity purification agents to purge CD6+ cells from donor materials, e.g., bone marrow, prior to transplantation using, e.g., cell separating, immuno-affinity columns. Patients whose bone marrow has been purged of T cells using unrelated anti-CD6 mAb to those of the invention have shown a significantly reduced incidence of both acute and chronic GVH disease, and do not require prophylactic treatment with immunosuppressive agents following transplantation (Soiffer et al., *J. Clin. Oncol.*, 10:1191 (1992), incorporated herein by reference in its entirety).

The following examples are offered by way of illustration, not by way of limitation.

EXAMPLE I

Domain Specificity of Known Anti-Human CD6 Monoclonal Antibodies

CD6 domain specificities of known anti-human CD6 antibodies were determined by ELISA assays to detect and quantify binding of the antibodies against a panel of truncated fusion proteins (Rg fusion proteins) that include one or more CD6 domains (D1, D2, D3 and stalk) fused to the hinge, CH2 and CH3 domains of human IgG1 in an ELISA assay. Production and purification of each Rg fusion protein used herein (CD6 SRCR domains incorporated within the various CD6-Rg fusion proteins employed are schematically depicted in FIG. 1) was conducted as disclosed in Bowen et al., *J. Biol. Chem.*, 271:17390–17396 (1996), incorporated herein by reference in its entirety.

Briefly, complementary DNA fragments encoding individual or groups of domains of human CD6 were produced by polymerase chain reaction methodology with oligonucleotides containing the appropriate restriction sites to mediate fusion with the thrombin-human IgG1 cassette (Rg fusion proteins) or the thrombin-mouse IgG2a cassette as described, e.g. in Aruffo et al., *Cell*, 61:1303–1313 (1990), and Kuener et al., *J. Immunol.*, 155:4917–4935 (1995), each incorporated herein by reference in its entirety.

The following CD6 fusions proteins, which also used the CD5 amino-terminal secretory sequence, contained the following amino acids according to the published sequences (Aruffo et al., *J. Exp. Med.*, 174:949–952 (1991)): CD6 Rg/mIgG2a, $Asp^{25}$-$Arg^{397}$; CD6D1-2 Rg, $Asp^{25}$-$Ala^{271}$; CD6D2-S Rg, $Glu^{158}$-$Arg^{397}$; CD6D2 Rg, $Glu^{168}$-$Ala^{271}$, CD6D3-S Rg, $Ser^{280}$-$Arg^{397}$, CD6D1-3 Rg was constructed as previously described by Wee et al., *Cell Immunol.*, 158:353–364 (1994), incorporated herein by reference in its entirety, and contained $Met^1$-$Ser^{361}$. The production of CD5 Rg was as described by Aruffo et al., *Cell*, 61:1303–1313 (1990), incorporated herein by reference in its entirety.

All CD6-Rg proteins were produced by transient transfection of COS cells and purified by protein A-Serpharose chromatography. Protein concentrations were determined using a Bradford dye binding procedure (Bio-Rad, Hercules, Calif.) against a mouse IgG protein standard. To analyze the fusion proteins, transiently transfected COS cells were pulsed with $^{35}$S translabel (Amersham Corp., Arlington Heights, Ill.) and purified proteins were analyzed by SDS-polyacrylamide gel electrophoresis.

To remove the Ig tail from CD6-Rg fusion proteins for stoichiometry of binding determinations, proteins are digested with thrombin (Sigma, St. Louis, Mo.) at a 50:1 (w/w) protein to thrombin ratio for 1 hr at room temperature. The Ig tails are then removed by affinity chromatography with protein A-Sepharose and analyzed by SDS-polyacrylamide gel electrophoresis.

To conduct ELISA assays for determining CD6 domain specificity of antibodies, Immulon II EIA plates (Dynatech Laboratories, Inc., Alexandria, Va.) were coated with 75 μl/well of a 200 ng/ml solution of each fusion protein in 0.05M sodium carbonate/sodium bicarbonate buffer, pH 9.6, and incubated overnight at 4° C. All subsequent steps were performed at room temperature. Coating agent was removed, the plates were washed twice with PBS containing 0.05% Tween 20 (PBS-Tween) and the wells blocked with blocking agent (specimen diluent (Genetic Systems Corp., Redmond, Wash.), diluted 1:10 in deionized water) for two hours. Blocking agent was removed and the wells washed twice with PBS-Tween.

Anti-CD6 antibodies were diluted to 5 μg/ml in specimen diluent, plated in duplicate (50 μl/well) on each of the fusion proteins and the plates incubated for 1 hour. Unbound antibody was aspirated and the plates washed four times with 300 μl/well of PBS-Tween after which 75 μl/well of horseradish peroxidase (HRP) conjugated goat anti-mouse IgG (Southern Biotech, Birmingham, Ala.) diluted in specimen diluent was added to all wells for one hour. Unbound HRP reagent was removed and the plates washed five times with PBS-Tween.

Bound HRP labeled reagent was detected by addition of 100 μl/well of tetramethylbenzidine (Genetic Systems Corp., Redmond, Wash.) diluted 1:100 in 0.1 M citrate buffer, pH 5.5, containing 0.015% of a 30% $H_2O_2$ solution. Plates were incubated for 15 minutes and the reaction stopped by the addition of 50 μl/well of 1N sulfuric acid. Optical density was measured at 450/630 nm on a Bio-Tek Instruments EL312 Microplate Reader.

Non-specific binding of anti-CD6 antibodies was controlled for in these ELISA assays by inclusion of an irrelevant but similarly constructed fusion protein comprised of the extracellular region of human CD40 fused to human IgG1(CD40-Rg).

Results of these assays are summarized in Table 1, below. Without exception, all antibodies reacted with the three fusion proteins that contained the first domain of CD6 but none of the remaining fusion proteins that contained various combinations of the second, third and stalk domains. This pattern of reactivity indicated that all the antibodies examined had specificity for the first domain of CD6.

TABLE 1

REACTIVITY OF COMMERCIAL AND LEUKOCYTE WORKSHOP ANTI-CD6 mAbs WITH TRUNCATED CD6 Rg FUSION PROTEINS

| mAb | Isotype | CD6 Rg | CD6D2-S Rg | CD6D3-S Rg | CD6D1-2 Rg |
| --- | --- | --- | --- | --- | --- |
| T12 | Mu IgM | 1.92 ± 0.03 | 0.04 ± 0.01 | 0.05 ± 0.00 | 1.89 ± 0.01 |
| MBG6 | Mu IgM | 0.92 ± 0.00 | 0.02 ± 0.00 | 0.01 ± 0.00 | 0.56 ± 0.03 |
| 24G4 | ? | 1.89 ± 0.01 | 0.18 ± 0.01 | 0.17 ± 0.00 | 1.76 ± 0.02 |
| F10-205-11 | Mu IgG2a | 1.86 ± 0.03 | 0.04 ± 0.00 | 0.04 ± 0.00 | 1.80 ± 0.04 |
| 12.1.5 | Mu IgG2a | 1.85 ± 0.00 | 0.12 ± 0.01 | 0.15 ± 0.01 | 1.78 ± 0.00 |
| G3-6 | ? | 1.87 ± 0.02 | 0.02 ± 0.01 | 0.01 ± 0.00 | 1.76 ± 0.03 |
| M-T605 | Mu IgG1 | 1.87 ± 0.02 | 0.02 ± 0.00 | 0.02 ± 0.00 | 1.79 ± 0.03 |
| ST23 | Mu IgG2a | 1.85 ± 0.00 | 0.02 ± 0.02 | 0.02 ± 0.00 | 1.78 ± 0.02 |
| M-T604 | Mu IgG2a | 2.14 ± 0.04 | 0.03 ± 0.00 | 0.03 ± 0.00 | 2.02 ± 0.01 |
| Tu33 | Mu IgG2a | 2.00 ± 0.03 | 0.02 ± 0.00 | 0.03 ± 0.00 | 1.89 ± 0.02 |
| BL-TP 6a | Mu IgG1 | 1.61 ± 0.06 | 0.01 ± 0.00 | 0.01 ± 0.00 | 1.49 ± 0.02 |
| M-T421 | Mu IgG1 | 2.10 ± 0.00 | 0.03 ± 0.00 | 0.03 ± 0.00 | 1.87 ± 0.06 |
| M-T211 | Mu IgG1 | 1.98 ± 0.00 | 0.01 ± 0.00 | 0.02 ± 0.01 | 1.89 ± 0.01 |
| M-T603 | Mu IgG1 | 2.11 ± 0.06 | 0.02 ± 0.01 | 0.03 ± 0.01 | 1.92 ± 0.00 |
| SPV-L14 | Mu IgG1 | 2.00 ± 0.00 | 0.01 ± 0.00 | 0.01 ± 0.00 | 1.91 ± 0.14 |
| MEM98 | Mu IgG1 | 1.96 ± 0.06 | 0.01 ± 0.00 | 0.01 ± 0.00 | 1.84 ± 0.02 |
| Lo-CD6-a | Rat IgG2a | 1.99 ± 0.10 | 0.02 ± 0.00 | 0.02 ± 0.00 | 1.84 ± 0.04 |

TABLE 1-continued

REACTIVITY OF COMMERCIAL AND LEUKOCYTE WORKSHOP
ANTI-CD6 mAbs WITH TRUNCATED CD6 Rg FUSION PROTEINS

| | | | | | |
|---|---|---|---|---|---|
| B-F3 | Mu IgG1 | 1.81 ± 0.01 | 0.05 ± 0.01 | 0.01 ± 0.010 | 1.70 ± 0.07 |
| UMCD6 | Mu IgG1 | 2.04 | 0.02 | 0.02 | 1.98 |
| M-T606 | Mu IgG2b | 0.06 ± 0.00 | 0.06 ± 0.07 | 0.02 ± 0.01 | 0.06 ± 0.04 |
| Mu anti-hCD6 polyclonal Serum | Mu IgG | 1.97 ± 0.028 | 1.86 ± 0.011 | 1.81 ± 0.01 | 1.87 ± 0.02 |

| mAb | CD6D2 Rg | CD6D1-3 Rg | CD40 Rg | Domain Assignment | Source |
|---|---|---|---|---|---|
| T12 | 0.04 ± 0.00 | 1.84 ± 0.01 | 0.03 ± 0.00 | D1 | ATCC |
| MBG6 | 0.02 ± 0.00 | 0.19 ± 0.00 | 0.02 ± 0.00 | D1 | Workshop |
| 24G4 | 0.21 ± 0.01 | 1.67 ± 0.03 | 0.20 ± 0.00 | D1 | Workshop |
| F10-205-11 | 0.05 ± 0.00 | 1.76 ± 0.05 | 0.04 ± 0.00 | D1 | Workshop |
| 12.1.5 | 0.20 ± 0.01 | 1.69 ± 0.02 | 0.16 ± 0.00 | D1 | Workshop |
| G3-6 | 0.02 ± 0.01 | 1.69 ± 0.01 | 0.01 ± 0.00 | D1 | Workshop |
| M-T605 | 0.02 ± 0.00 | 1.68 ± 0.01 | 0.01 ± 0.00 | D1 | Pharmingen |
| ST23 | 0.02 ± 0.01 | 1.74 ± 0.01 | 0.01 ± 0.00 | D1 | Biomeda |
| M-T604 | 0.04 ± 0.00 | 2.03 ± 0.03 | 0.02 ± 0.00 | D1 | Connex |
| Tu33 | 0.02 ± 0.00 | 1.89 ± 0.03 | 0.01 ± 0.00 | D1 | Biogenesis |
| BL-TP 6a | 0.01 ± 0.00 | 1.35 ± 0.02 | 0.01 ± 0.00 | D1 | Sanbio |
| M-T421 | 0.03 ± 0.00 | 1.77 ± 0.01 | 0.06 ± 0.00 | D1 | Connex |
| M-T211 | 0.01 ± 0.00 | 1.62 ± 0.01 | 0.03 ± 0.01 | D1 | Connex |
| M-T603 | 0.02 ± 0.00 | 1.85 ± 0.02 | 0.07 ± 0.00 | D1 | Connex |
| SPV-L14 | 0.01 ± 0.00 | 1.74 ± 0.14 | 0.01 ± 0.00 | D1 | Zymed |
| MEM98 | 0.01 ± 0.00 | 1.84 ± 0.03 | 0.01 ± 0.00 | D1 | Harlan/Sera-Lab |
| Lo-CD6-a | 0.03 ± 0.00 | 1.61 ± 0.05 | 0.03 ± 0.00 | D1 | Biosource |
| B-F3 | 0.02 ± 0.00 | 1.62 ± 0.07 | 0.01 ± 0.00 | D1 | Biosource |
| UMCD6 | 0.02 | 1.83 | 0.02 | D1 | Ancell |
| M-T606 | 0.01 ± 0.00 | 0.06 ± 0.01 | 0.04 ± 0.01 | Not Active | Connex |
| Mu anti-hCD6 polyclonal Serum | 1.83 ± 0.02 | 1.83 ± 0.00 | 0.03 ± 0.00 | | |

EXAMPLE II
Testing of Known Anti-Human CD6 Monoclonal Antibodies for Blocking Activity Against CD6/ALCAM Binding Interactions Each of the known antibodies assayed above for CD6 domain specificity and shown to bind the first domain of CD6 were further evaluated for their capacity to inhibit binding of an ALCAMRg fusion protein to cells expressing CD6, as a measure of their ability to inhibit CD6/ALCAM interactions. HPB-ALL cells (a CD6+ human T cell leukemia line) were added to duplicate round-bottom 96-well plates (Corning, Ithaca, N.Y.), 2×10$^5$/well, and the plates centrifuged at 250 xg for 5 minutes at 4° C. Culture media was removed and anti-CD6 mAbs, diluted to 20 µg/ml in IMDM containing 10% (v/v) FCS (10% FCS-Iscove's), were added to wells on both plates, 50 µl/well. A 1:100 dilution of sera from a mouse immunized with humanCD6-mIg (see immunization section), served as a positive control while normal mouse sera, anti-human CD4 (Immunotech, Westbrode, Me.) and anti-human CD71 (Immunotech) were included as negative controls. Following a 30 minute incubation on ice, 2% FCS-Iscove's was added to all wells, 150 µl/well, and the plates were centrifuged at 250 xg for 5 minutes at 4° C. Following removal of the antibodies, wells on one plate received 50 µl of a 1:200 dilution (in 2% FCS-Iscove's) of phycoerythrin (PE) conjugated goat anti-murine IgG (Southern Biotechnology) while wells on the second plate received 50 µl of a 1 µg/ml solution of soluble ALCAM-Ig fusion protein (ALCAM VVCC Rg; Bowen et al., J. Biol. Chem., 1996). Plates were incubated on ice for 30 minutes after which cold 2% FCS-Iscove's was added to all wells, 150 µl/well, and the plates again centrifuged at 250 g for 5 minutes at 4° C. Unbound PE reagent on the first plate was removed, the cells were washed an additional two times with cold 2% FCS-Iscove's and left resuspended in 200 µl/well of cold 2% FCS-Iscove's. Unbound ALCAM-Ig fusion protein on the second plate was removed and 50 µl of a 1:100 dilution of fluoroscein isothiocyanate (FITC) conjugated donkey anti-human IgG (Jackson Immuno Research, Inc., West Grove, Pa.) was added to all wells. After an additional 30 minute incubation on ice, the wells were washed three times with cold 2% FCS-Iscove's and left resuspended in 200 µl/well of cold 2% FCS-Iscove's. Cells from both plates were subsequently analyzed by flow cytometry on a FACScan (Becton Dickinson, Mountain View, Calif.) for specific mAb binding (PE signal-first plate) and mAb mediated blocking of ALCAM-Ig interaction with the cells (FITC signal-second plate).

Results of this analysis are shown in Table 2, below. With the exception of mAb MBG6, which was weak on the domain mapping experiment and may have lost activity by the time the current assay was performed, all the anti-CD6 antibodies and the immune mouse serum stained the HPB-ALL cells quite well. However, only the immune mouse serum was capable of blocking the binding of the ALCAM fusion protein to these cells.

TABLE 2

SUMMARY OF THE BINDING AND BLOCKING
CHARACTERISTICS OF NOVEL ANTI-CD6 MABS

| Source | Monoclonal Antibody | Binding of Antibody to HPB-ALL Cells* | % Inhibition of ALCAM Rg Binding to HPB-ALL Cells |
|---|---|---|---|
| | Medium | 0 | 0% |
| Biomeda | ST23 | 225 | −35% |
| Pharmingen | M-T605 | 283 | −58% |
| Connex | M-T604 | 242 | 18% |
| Sanbio | BL-TP6a | 188 | −17% |
| Biogenesis | Tu-33 | 236 | −35% |
| Biosource | B-F3 | 242 | −19% |
| Harlan | MEM98 | 283 | −91% |
| Zymed | SPV-L14 | 334 | −49% |
| Ancell | UMCD6 | 271 | −77% |
| Connex | M-T603 | 276 | −108% |
| Connex | M-T211 | 203 | −94% |
| Connex | M-T606 | 401 | −1% |
| Connex | M-T421 | 285 | −76% |
| Biosource | L0-CD6-a | 279 | −85% |
| Leukocyte Workshop | G3-6 | 269 | −66% |
| Leukocyte Workshop | 12.1.5 | 241 | −17% |
| Leukocyte Workshop | F10-205-11 | 315 | −5% |
| Leukocyte Workshop | 24G4 | 202 | 0% |
| Leukocyte Workshop | MBG6 | −15 | 14% |
| ATCC | T12 | 319 | −87% |
| | anti-CD4 | 391 | 0% |
| | anti-HLA A,B,C | 345 | −5% |
| | normal mouse serum | 14 | 13% |
| | mouse anti-huCD6-mIg serum | 343 | 82% |

*Mean fluorescence intensity of primary antibody binding minus mean fluorescence intensity of secondary antibody only.
**Negative percent inhibition reflects enhanced ALCAM Rg binding compared to that seen with no primary antibody (medium only).

EXAMPLE III
Production and Selection of Anti-Human CD6 mAbs

A. Immunization

6–8 week old female BALB/c mice (Taconic, Germantown, N.Y.) were immunized with a purified, recombinant human CD6-Rg fusion protein consisting of the extracellular three SRCR domains and the short membrane proximal stalk domain of human CD6 fused to the hinge, CH2 and CH3 domains of a murine IgG2a antibody (hCD6-mIg) (Bowen et al., *J. Biol. Chem.*, supra). Primary immunization was administered intraperitoneally with an emulsion (total of 100 μl) of 25 μg protein in Ribi adjuvant (R-730; Ribi ImmunoChem Research, Inc., Hamilton, Mont.). A similar immunization but with 50 μg protein was performed on day 19. On day 30, one mouse received an intravenous pre-fusion booster injection of 50 μg of protein in 100 μl of phosphate buffered saline (PBS). This animal was used for the first fusion (H6-1). On day 37, another mouse received an identical booster immunization and was utilized for the second fusion (H6-2). Serum samples obtained from these latter two mice one week after their second immunization contained significant titers of IgG antibody specific for the human CD6 portion of the fusion protein as indicated in an ELISA performed with hCD6-hIg (Bowen et al., supra) and an irrelevant but similarly constructed fusion protein, hCD40-hIg (Hollenbaugh et al., *EMBO J.* 11:4313–4321 (1992).

B. Fusion

Three days after the pre-fusion booster, cells were harvested from the spleen and all identifiable lymph nodes and were fused at a 3:1 ratio of leukocytes: myeloma cells with P3X63-Ag8.653 myeloma cells (Kearney et al., *J. Immunol.* 123:1548–1550 (1979), according to the method of Lane, *J. Immunol. Methods*, 81:223–228 (1985), each incorporated herein by reference in its entirety). In the case of H6-1 the resulting post-fusion cell suspension was seeded into 15 96-well culture plates at a density of approximately $1.04 \times 10^5$ cells/well in the presence of hybridoma growth media (Iscove's Modified Dulbecco's Medium supplemented with 10% fetal calf serum, 2 mM L-glutamine, 100 U/ml penicillin, 100 μg/ml streptomycin, 10% hybridoma cloning factor (BM-Condimed® H1; Boehringer Mannheim, Indianapolis, Ind.), and HAT (100 uM hypoxanthine; 0.4 uM aminopterin; 16 uM thymidine). Wells were fed on days 3 and 6 post fusion by replacement of half the supernatant with fresh hybridoma medium and assayed for anti-human CD6 specific antibody on day 9. For H6-2, the post-fusion cell suspension was seeded into 20 96-well plates at a density of approximately $1.24 \times 10^5$ cells/well in hybridoma growth media. Wells were fed on days 4 and 6 post fusion and assayed for specific antibody on day 8.

C. Screening

1. Identification of hCD6 Specific Wells a) H6-1 Fusion

Cell culture supernatants from all wells were initially screened for specific reactivity to human CD6 by analysis of their ability to bind to a human CD6-Ig fusion protein in an ELISA assay. The human CD6-Ig protein was essentially identical to hCD6-mIg used for immunization of mice except that the murine hinge, CH2 and CH3 regions were replaced with the hinge, CH2 and CH3 domains of human IgG1 (CD6 Rg; Bowen et al., supra).

For the assay of H6-1, Immulon II EIA plates (Dynatech Laboratories, Inc., Alexandria, Va.) were coated with 75 μl/well of a 500 ng/ml solution of CD6Rg in 0.05M sodium carbonate/sodium bicarbonate buffer, pH 9.6, and incubated overnight at 4° C. All subsequent steps were performed at room temperature. Coating agent was removed and the wells blocked with blocking agent (specimen diluent (Genetic Systems Corp., Redmond, Wash.), diluted 1:10 in deionized water) for one hour. Blocking agent was removed and the wells washed twice with PBS containing 0.05% Tween 20 (PBS-Tween). Culture supernatants were then replica plated onto the assay plates, 50 μl/well, and the plates incubated for 1 hour. Supernatants were aspirated and the plates washed once with 150 μl/well of PBS containing 1% FCS. Following removal of the culture supernatants, the wells were washed three times with PBS-Tween and then 75 μl/well of horseradish peroxidase (HRP) conjugated goat anti-mouse IgG (Biosource International, Inc., Camarillo, Calif.) diluted in specimen diluent was added to all wells for one hour. Unbound HRP reagent was removed and the plates washed four times with PBS-Tween. Bound HRP labeled reagent was visualized by addition of 100 μl/well of tetramethylbenzidine (Genetic Systems Corp., Redmond, Wash.) diluted 1:100 in 0.1 M citrate buffer, pH 5.5, containing 0.015% of a 30% $H_2O_2$ solution. Plates were incubated for 15 minutes and the reaction stopped by the addition of 50 μl/well of 3N sulfuric acid. Optical density was measured at 450/630 nm on a Bio-Tek Instruments EL312 Microplate Reader.

Figure 2A:
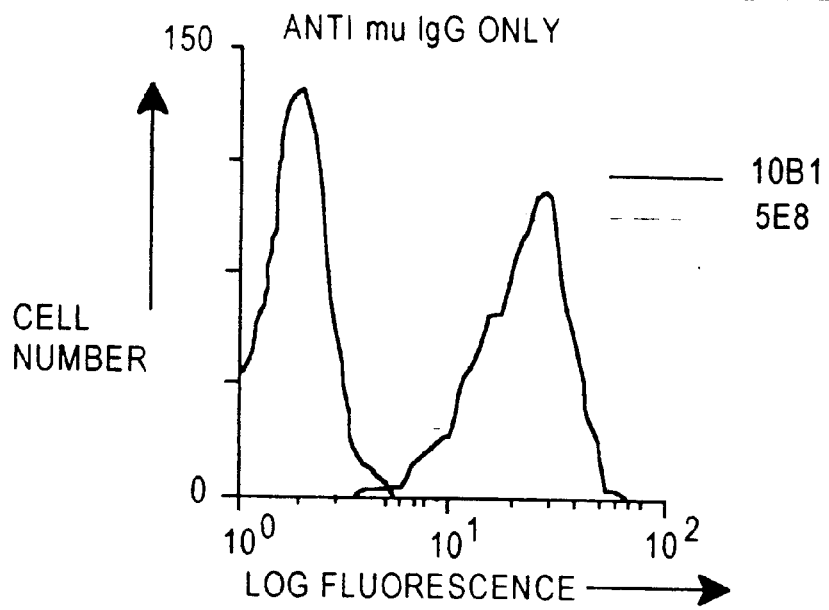
FIGS. 2A and 2B depict flow cytometric scans to detect specific binding activity of antibodies to CD6+ cells and antibody mediated blocking of ALCAM-Ig interaction with the cells.
Figure 2B:
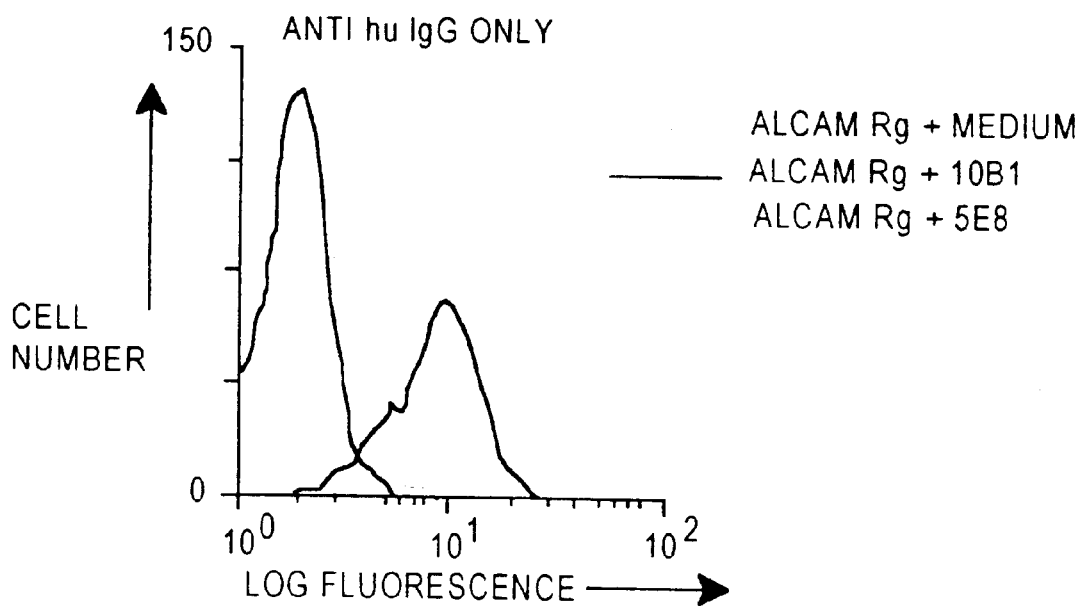
Figure 3A:
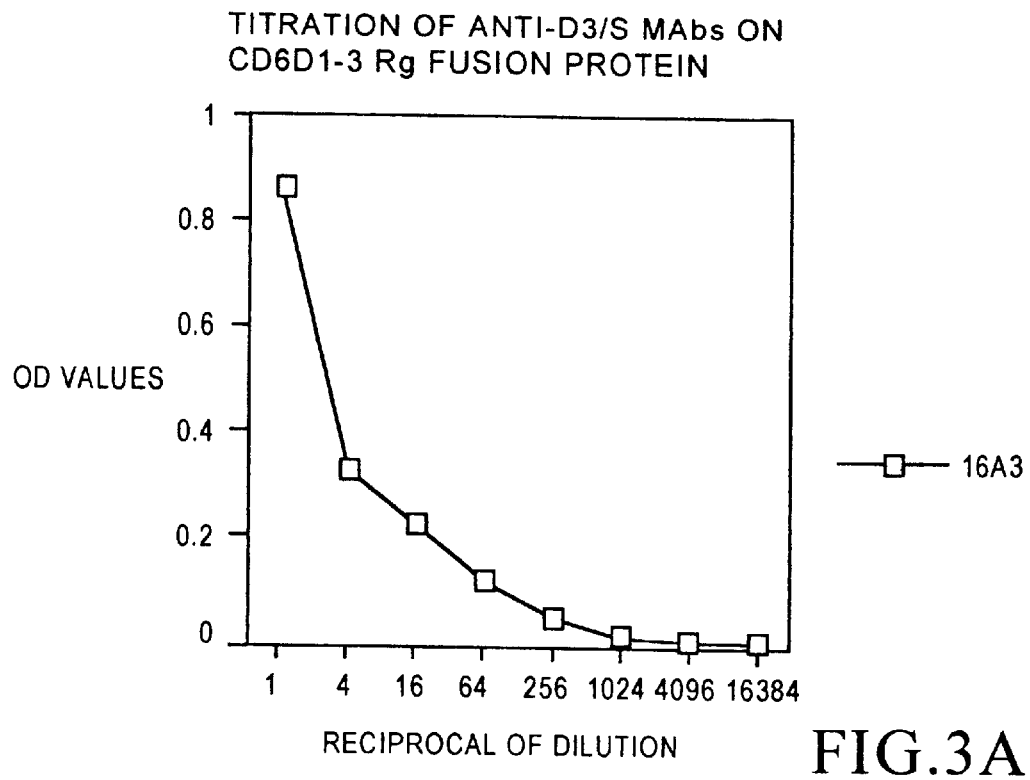
FIGS. 3A–3D and 4A–4C depict titration curves for exemplary anti-human CD6D3/anti-human CD6S monoclonal antibodies on CD6D1-3 Rg fusion protein.
Figure 3B:
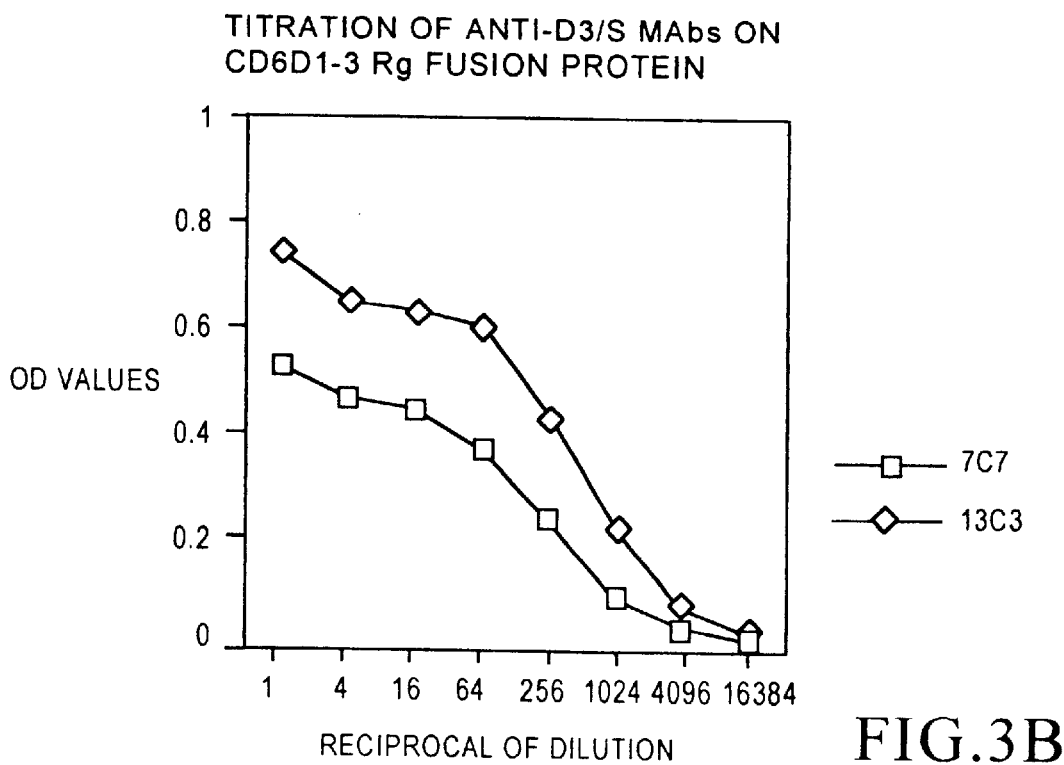
Figure 3C:
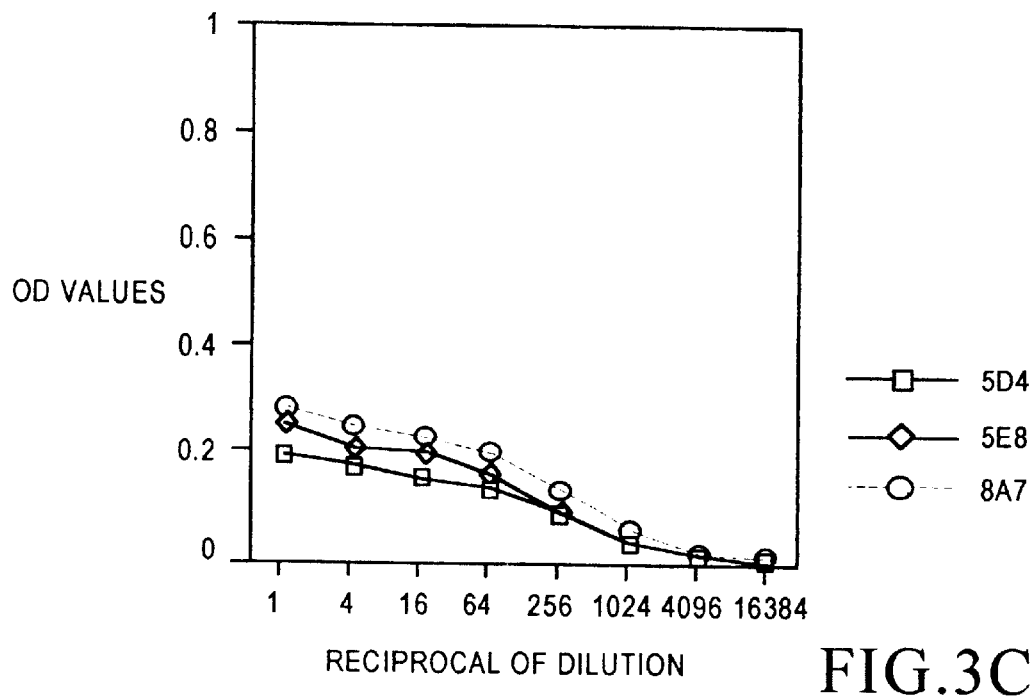
Figure 3D:
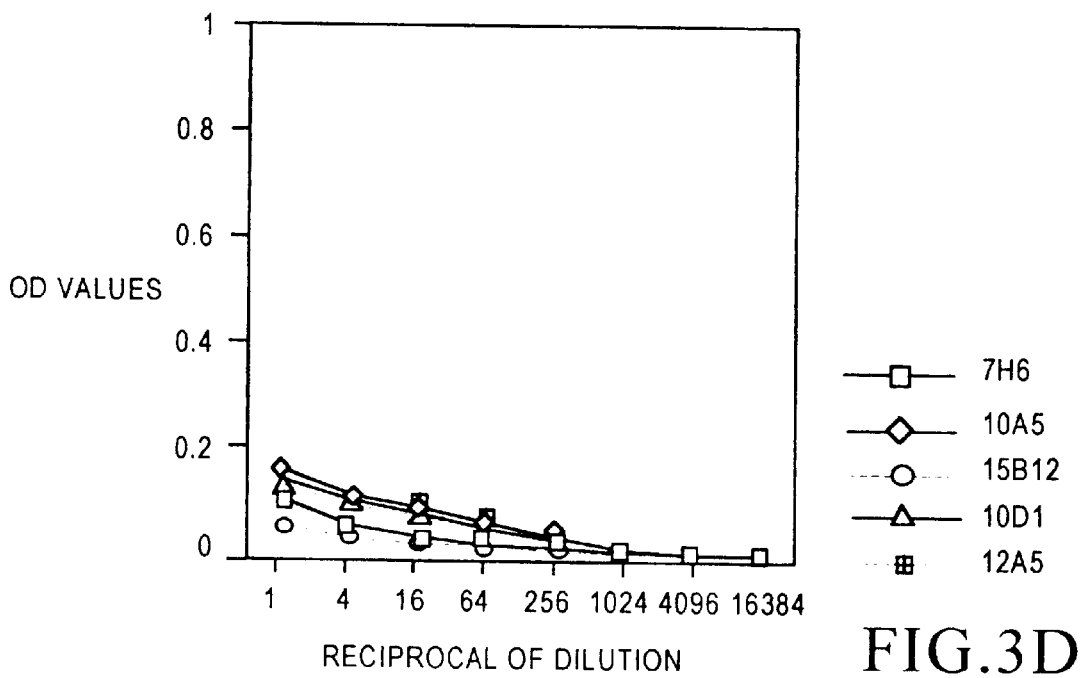

Supernatants from wells that reacted with hCD6-hIg were next evaluated for their ability to bind to CD6+ cells and to block the interaction of ALCAM with CD6+ cells. Binding and blocking were initially examined in the same assay. In later assays, they were assessed independently. The initial assay employed HPB-ALL cells, a human T cell leukemia line that we had previously shown to express high levels of CD6. Cells were added to round-bottom 96-well plates (Corning, Ithica, N.Y.), $1\times10^5$/well, and the plates centrifuged at 250 xg for 5 minutes at 40° C. Culture media was removed and cold hybridoma supernatants were added to individual wells, 50 μl/well. Following a 30 minute incubation on ice, cold IMDM containing 2% (v/v) FCS (2% FCS-Iscove's) was added to all wells, 150 μl/well, and the plates were centrifuged at 250 xg for 5 minutes at 4° C. Following removal of the supernatants, each well received 50 μl of a 1:200 dilution (in 2% FCS-Iscove's) of phycoerythrin (PE) conjugated goat anti-murine IgG (Southern Biotechnology) and 50 μl of a 1 μg/ml solution of soluble ALCAM-Ig fusion protein (ALCAM VVCC Rg; Bowen et al., supra). Plates were incubated on ice for 30 minutes after which cold 2% FCS-Iscove's was added to all wells, 150 μl/well, and the plates again centrifuged at 250 xg for 5 minutes at 4° C. Unbound PE reagent and ALCAM-Ig fusion protein were removed and 50 μl of a 1:100 dilution of fluoroscein isothiocyanate (FITC) conjugated donkey anti-human IgG [(Jackson Immuno Research, Inc., West Grove, Pa.), was added to all wells. After an additional 30 minute incubation on ice, the wells were washed three times with cold 2% FCS-Iscove's and left resuspended in 200 μl/well of cold 2% FCS-Iscove's. Cells were subsequently analyzed by flow cytometry on a FACScan (Becton Dickinson, Mountain View, Calif.) for specific mAb binding (PE signal) and mAb mediated blocking of ALCAM-Ig interaction with the cells (FITC signal). By this means, a number of the ELISA positive wells were shown to not bind CD6+ cells indicating that the antibodies recognized a non-native form of CD6 or the Ig tail on the fusion protein. The majority of supernatants, however, did bind to the cells and amongst these approximately 35% further showed greater than 24% inhibition of ALCAM-Ig binding. By way of example, FIGS. 2A and 2B demonstrate that while master well supernatants 10B1 and 5E8 both stained the HPB-ALL cells brightly, only 5E8 was capable of effectively blocking the interaction of ALCAM-Ig with these cells.

b) H6-2 Fusion

The primary screen of supernatants for H6-2 was similar to that for H6-1 except that it was designed to more easily identify those wells that contained anti-CD6 antibody specific for the second or third domains of CD6 as opposed to the first domain. Three of the 20 fusion plates were screened on CD6Rg exactly as described above except that the coating concentration of protein was 200 ng/ml. Of the remaining plates, nine were screened on CD6D2-S Rg (containing the second and third extracellular SRCR domains and the short membrane proximal stalk domain of CD6) while the other eight were assayed on CD6D3-S Rg (containing the third extracellular SRCR domain and the stalk domain of CD6). Both truncated proteins were coated on plates at a concentration of 200 ng/ml. Other than this modification, the assay was performed as described above. All supernatants that reacted with any of the tested fusion proteins were then tested for their ability to bind to CD6+ cells and to block the interaction of ALCAM with CD6+ cells as described for H6-1. Results were quite similar to those in H6-1 with approximately 24% of the fusion protein positive wells exhibiting greater than 25% inhibition of ALCAM Rg binding.

EXAMPLE IV

Domain Specificity of Novel Anti-Human CD6 Monoclonal Antibodies

Initial domain specificity tests were carried out with those master well supernatants identified above that exhibited the most complete inhibition of ALCAM Rg binding to HPB-ALL cells. To determine which domain(s) of CD6 these antibody-containing supernatants exhibit specific binding against, they were next evaluated using the same ELISA on a panel of truncated CD6 Rg fusion proteins that was utilized previously to assign domain specificity to the commercially available and workshop anti-CD6 mAbs. Ten master well supernatants were tested, each at neat concentration and in duplicate. Results are shown in Table 3, below. Supernatants from wells H6-1.7H6, H6-2.8A7, H6-2.10D1, H6-2.13C3, H6-2.16A3 and H6-2.15B12 did not react with CD6D1-2 Rg or CD6D2 Rg but strongly recognized CD6D3-S Rg, CD6D2-S Rg and CD6 Rg. This reactivity profile suggested that the epitope recognized by each of these antibodies was located in the third membrane-proximal SRCR domain, the stalk domain or at a site composed of elements of both these domains. Of note, each of these supernatants reacted weakly or not at all with CD6D1-3 Rg. This observation in combination with the other fusion protein data would ostensibly argue for placement of the reactive epitope of these antibodies primarily in the stalk region. However, since the human CD6D1-3 Rg protein has been previously been shown to bind with approximately 1000-fold less affinity than CD6-Rg to ALCAM (Bowen et al., *J. Biol. Chem.* 271:17390–17396 (1996)) it is likely that the CD6D1-3 Rg protein used in this study may have been conformationally compromised, particularly in the third domain (see below). Thus, domain assignment to the third domain with regards to these first six antibodies can not be ruled out.

Supernatants from the remaining four master wells displayed a somewhat more complicated reactivity profile. The profile for master well H6-2.5D4 was quite similar to that described above except for the addition of weak reactivity with the CD6D2 Rg and possibly CD6D1-2 Rg proteins, suggesting the likely presence of two anti-CD6 antibodies; one with specificity for the D3/S domains and another very low titered antibody directed against the second domain. The profiles for master wells H6-2.5E8, H6-2.7C7 and H6-2.12A5 were very similar to each other in that all the fusion proteins were recognized except for CD6D2 Rg. This complex profile was most compatible with the presence of one antibody specific for the D3/S domains and one with specificity for the first SRCR domain of CD6.

Based on the foregoing reactivity profiles, all ten CD6/ ALCAM blocking master well supernatants displayed strong reactivity against fusion proteins that contained, at a minimum, the third SRCR and stalk domains of CD6. This observation indicates that the antibodies identified herein as having blocking activity against human CD6/ALCAM interactions bind specifically to epitopes within the membrane-proximal D3-S domains of CD6. This observation is further supported by similar domain specificity mapping for the remaining master well supernatants from H6-1 and H6-2. Without exception, every supernatant that demonstrated capacity to inhibit binding of ALCAM Rg to HPB-ALL cells was also reactive with the CD6D3-S Rg fusion protein. Likewise, no supernatant that clearly showed specificity for only the first or second SRCR domains, or for a combination of the two, was able to inhibit the interaction of ALCAM Rg with CD6.

TABLE 3

REACTIVITY OF BLOCKING ANTI-CD6 MASTER WELL SUPERNATANTS
WITH TRUNCATED CD6 RG FUSION PROTEINS

| MAb | CD6 Rg | CD6D2-S Rg | CD6D3-S Rg | CD6D1-2 Rg | CD6D2 Rg | CD6D1-3 Rg |
|---|---|---|---|---|---|---|
| H6-1.7H6 | 1.67 ± 0.03 | 1.63 ± 0.02 | 1.66 ± 0.00 | 0.02 ± 0.00 | 0.02 ± 0.00 | 0.02 ± 0.00 |
| H6-2.5D4 | 1.87 ± 0.01 | 1.84 ± 0.02 | 1.94 ± 0.04 | 0.05 ± 0.01 | 0.13 ± 0.01 | 0.09 ± 0.00 |
| H6-2.5E8 | 1.67 ± 0.05 | 1.67 ± 0.09 | 1.63 ± 0.01 | 0.94 ± 0.04 | 0.01 ± 0.00 | 0.95 ± 0.00 |
| H6-2.7C7 | 1.62 ± 0.00 | 1.61 ± 0.01 | 1.55 ± 0.11 | 0.76 ± 0.03 | 0.02 ± 0.00 | 0.55 ± 0.02 |
| H6-2.8A7 | 1.67 ± 0.02 | 1.60 ± 0.03 | 1.62 ± 0.08 | 0.01 ± 0.00 | 0.01 ± 0.00 | 0.08 ± 0.00 |
| H6-2.10D1 | 1.66 ± 0.01 | 1.58 ± 0.01 | 1.51 ± 0.05 | 0.02 ± 0.01 | 0.02 ± 0.00 | 0.04 ± 0.00 |
| H6-2.12A5 | 1.64 ± 0.03 | 1.50 ± 0.03 | 1.52 ± 0.05 | 0.82 ± 0.03 | 0.01 ± 0.00 | 0.83 ± 0.02 |
| H6-2.13C3 | 1.64 ± 0.02 | 1.69 ± 0.04 | 1.65 ± 0.01 | 0.03 ± 0.00 | 0.03 ± 0.01 | 0.18 ± 0.00 |
| H6-2.15B12 | 1.69 ± 0.09 | 1.57 ± 0.01 | 1.53 ± 0.00 | 0.02 ± 0.00 | 0.02 ± 0.00 | 0.02 ± 0.00 |
| H6-2.16A3 | 1.88 ± 0.02 | 1.85 ± 0.04 | 1.82 ± 0.08 | 0.03 ± 0.01 | 0.03 ± 0.00 | 0.08 ± 0.00 |
| Mu anti-hCD6 Polyclonal Serum | 1.82 ± 0.13 | 1.75 ± 0.06 | 1.58 ± 0.06 | 1.86 ± 0.04 | 1.69 ± 0.01 | 1.71 ± 0.01 |

Bold Print = Positive = $OD_{450/630} \geq 0.15$

Specific antibody producing hybridomas in each of the above noted master wells were then cloned by limiting dilution in hybridoma growth media lacking HAT. Resulting clones from wells H6-2.5E8, H6-2.7C7 and H6-2.12A5 were screened by ELISA on both the full-length CD6 Rg and CD6D3-S Rg proteins. Clones that were positive on the former and negative on the latter fusion proteins were provisionally assumed to have specificity for the first SRCR domain of CD6 while those that reacted with both proteins were assigned a D3-S specificity. Clones from the remaining master wells were screened by ELISA only on the CD6D3-S Rg fusion protein. Clones specific for D1 or D3-S were isolated from master wells H6-2.7C7 and H6-2.12A5. The other master wells yielded only anti-D3-S specific clones. Representative clones from each master well that were reactive with the CD6D3-S Rg fusion protein were then examined on the full panel of CD6 fusion protein by ELISA in order to assign their domain specificity. Results of this analysis are shown in Table 4, below along with those obtained for another anti-D3/S mAb (H6-2.10A5) that was isolated while cloning mAbs specific for the second SRCR domain of CD6 (see Example 7). All the mAbs, as expected, recognized the CD6 Rg, CD6D2-S Rg and CD6D3-S Rg proteins but were unreactive with CD6D1-2 Rg, CD6D2 Rg and the irrelevant control CD40 Rg protein, a pattern consistent with a domain specificity assignment to the third SRCR and/or stalk domains of CD6. Similar to what was observed in the original domain specificity tests on the master wells that yielded these anti-D3/S mAbs, reactivity of the cloned mAbs with the CD6D1-3 Rg protein was again weak to very weak compared to the other third SRCR domain containing proteins. Binding of mAbs 5D4, 5E8, 7C7, 8A7, 13C3 and 16A3 to CD6D1-3 Rg was significant enough to conclude that these mAbs are specific for the third SRCR domain, as opposed to the stalk region. For the remaining mAbs, specificity was determined only to the level of assignment to the CD6D3-S domains collectively, leaving the possibility that these antibodies recognize epitopes within CD6D3, CD6S, or overlapping the junction of the two domains. The domain specificity assignments for all the anti-D3/S mAbs are summarized in Table 5. Included on this table are results of an isotype analysis performed on each mAb using the IsoStrip test kit (Boehringer Mannheim, Indianapolis, Ind.). With the exception of 5D4 (an $IgG_{2a}$) and 16A3 (an $IgG_{2b}$), all possessed an $IgG_1$ isotype.

TABLE 4

REACTIVITY OF ANTI-CD6 DOMAIN 3/S MAbs WITH TRUNCATED CD6 Rg FUSION PROTEINS

| MAb | CD6 Rg | CD6D2-S Rg | CD6D3-S Rg | CD6D1-2 Rg | CD6D2 Rg | CD6D1-3 Rg | CD40 Rg |
|---|---|---|---|---|---|---|---|
| H6-1.7H6 | 1.93 ± 0.06 | 1.86 ± 0.09 | 1.80 ± 0.02 | 0.02 ± 0.00 | 0.03 ± 0.00 | 0.06 ± 0.00 | 0.02 ± 0.00 |
| H6-2.5D4 | 2.02 ± 0.05 | 1.93 ± 0.04 | 1.93 ± 0.02 | 0.01 ± 0.00 | 0.02 ± 0.00 | 0.23 ± 0.00 | 0.02 ± 0.00 |
| H6-2.5E8 | 1.90 ± 0.04 | 1.86 ± 0.05 | 1.82 ± 0.06 | 0.02 ± 0.00 | 0.02 ± 0.00 | 0.40 ± 0.00 | 0.01 ± 0.00 |
| H6-2.7C7 | 1.89 ± 0.10 | 1.93 ± 0.03 | 1.84 ± 0.02 | 0.02 ± 0.00 | 0.02 ± 0.00 | 0.63 ± 0.05 | 0.01 ± 0.00 |
| H6-2.8A7 | 1.82 ± 0.02 | 1.89 ± 0.01 | 1.80 ± 0.00 | 0.02 ± 0.02 | 0.02 ± 0.00 | 0.38 ± 0.01 | 0.02 ± 0.00 |
| H6-2.10A5 | 1.80 ± 0.07 | 1.79 ± 0.03 | 1.79 ± 0.01 | 0.01 ± 0.00 | 0.01 ± 0.00 | 0.09 ± 0.00 | 0.01 ± 0.00 |
| H6-2.10D1 | 1.82 ± 0.01 | 1.75 ± 0.01 | 1.80 ± 0.03 | 0.01 ± 0.00 | 0.02 ± 0.00 | 0.15 ± 0.01 | 0.02 ± 0.00 |
| H6-2.12A5 | 1.76 ± 0.01 | 1.83 ± 0.04 | 1.73 ± 0.02 | 0.01 ± 0.00 | 0.02 ± 0.00 | 0.15 ± 0.00 | 0.01 ± 0.00 |
| H6-2.13C3 | 1.80 ± 0.14 | 1.85 ± 0.03 | 1.76 ± 0.00 | 0.01 ± 0.00 | 0.02 ± 0.00 | 0.79 ± 0.02 | 0.01 ± 0.00 |
| H6-2.15B12 | 1.90 ± 0.02 | 1.94 ± 0.02 | 1.86 ± 0.07 | 0.02 ± 0.01 | 0.02 ± 0.00 | 0.04 ± 0.00 | 0.02 ± 0.00 |
| H6-2.16A3 | 2.04 ± 0.00 | 2.00 ± 0.01 | 1.96 ± 0.02 | 0.04 ± 0.00 | 0.05 ± 0.00 | 0.34 ± 0.01 | 0.04 ± 0.00 |
| Mu anti-hCD6 Polyclonal Serum | 2.05 ± 0.02 | 1.98 ± 0.05 | 1.82 ± 0.00 | 2.01 ± 0.04 | 1.90 ± 0.05 | 1.94 ± 0.04 | 0.05 ± 0.00 |

Bold Print = Positive = $OD_{450/630} \geq 0.15$

TABLE 5

ANTI-HUMAN CD6 MAbs

| MAb | Isotype | Domain Specificity |
|---|---|---|
| H6-1.5E1-2A9 | IgG1 | D2 |
| H6-2.5F7-2E5 | IgG1 | D2 |
| H6-1.12F10-2E11 | IgG1 | D2 |
| H6-2.14H2-1F3 | IgG1 | D2 |
| H6-1.15D7-1B11 | IgG1 | D2 |
| H6-1.7H6-2A11 | IgG1 | D3-S |
| H6-2.5D4-2D11 | IgG2a | D3-S |
| H6-2.5E8-2D1 | IgG1 | D3-S |
| H6-2.6D12-1A7 | IgG1 | D3-S |
| H6-2.7C7-1E2 | IgG1 | D3-S |
| H6-2.8A7-2C7 | IgG1 | D3-S |
| H6-2.10A5-1D2 | IgG1 | D3-S |
| H6-2.10D1-1H10 | IgG1 | D3-S |
| H6-2.12A5-1C6 | IgG1 | D3-S |
| H6-2.13C3-1A11 | IgG1 | D3-S |
| H6-2.15B12-2F8 | IgG1 | D3-S |
| H6-2.16A3-1D1 | IgG1 | D3-S |
| H6-2.19D7-2A10 | IgG1 | D3-S |

An evaluation of the ability of the clonal anti-D3/S supernatants to bind to CD6+ cells and to inhibit the binding of ALCAM Rg to CD6+ cells as described earlier for the commercial/workshop anti-CD6 mAbs is shown in Table 6. All stained the CD6+ cells at roughly comparable levels and the level of staining observed was similar to that seen with several commercial anti-SRCR domain 1 mAbs. Additionally, all completely blocked the interaction of ALCAM Rg with CD6+ HPB-ALL cells, in marked contrast to what was seen with anti-SRCR domain 1 mAbs in Example I, above.

TABLE 6

SUMMARY OF THE BINDING AND BLOCKING CHARACTERISTICS OF NOVEL ANTI-DOMAIN 2 AND DOMAIN 3/STALK MAbs

| Monoclonal Antibody | Domain | Binding of Antibody to HPB-ALL Cells* | % Inhibition** of ALCAM Rg Binding to HPB-ALL Cells |
|---|---|---|---|
| Secondary Antibody Only | | 0 | 1% |
| H6-2.15B12 | 3/S | 256 | 102% |
| H6-2.16A3 | 3 | 243 | 102% |
| H6-2.7C7 | 3 | 267 | 102% |
| H6-2.10A5 | 3/S | 269 | 102% |
| H6-2.5D4 | 3 | 213 | 105% |
| H6-2.7H6 | 3/S | 293 | 101% |
| H6-2.10D1 | 3/S | 268 | 97% |
| H6-2.8A7 | 3 | 272 | 100% |
| H6-2.13C3 | 3 | 263 | 102% |
| H6-2.5E8 | 3 | 263 | 101% |
| H6-2.12A5 | 3/S | 266 | 102% |
| H6-1.15D7 | 2 | 272 | −52% |
| H6-1.5E1 | 2 | 266 | −66% |
| H6-1.12F10 | 2 | 297 | −39% |
| H6-2.12H2 | 2 | 266 | −41% |
| H6-2.5F7 | 2 | 257 | −49% |
| SPV-L14 | 1 | 334 | −49% |
| UMCD6 | 1 | 271 | 77% |
| ST23 | 1 | 225 | −35% |
| PA9-IIIH10 | | 0 | 11% |
| EXA-2.1H8 | | 17 | 7% |
| PA9-IVA7 | | 5 | 10% |

*Mean fluorescence intensity of antibody binding minus mean fluorescence intensity of secondary antibody only binding to HPB-ALL cells.
**Negative percent inhibition reflects enhanced ALCAM Rg binding compared to that seen with no primary antibody (medium only).

EXAMPLE V

Binding Subgroups Among Anti-Human CD6D3-S mAbs

The variable binding of the anti-D3/S mAbs to the CD6D1-3 Rg protein suggested that some of these mAbs recognized different epitopes within the D3/S domains. To clarify these binding subgroups, each mAb supernatant was titrated by serial four-fold dilution against the CD6D1-3 Rg protein using the ELISA format outlined earlier for domain specificity testing. Preliminary analysis of antibody concentration in each supernatant using an anti-murine Ig sandwich ELISA had indicated that there was no more than a four-fold difference in Ig concentration between supernatants. Therefore, major differences in the titration profiles of the antibodies were considered to be most likely due to recognition of different epitopes within the fusion protein.

Titration profiles for different anti-CD6D3/S antibodies, using an anti-murine IgG Fc specific second step reagent to monitor mAb binding, are shown in FIGS. 3A–3D. Mab 16A3 clearly had a unique titration curve while mAbs 7C7 and 13C3 appeared similar based on the shape of their curves and their greater reactivity with CD6D1-3 Rg. The remaining mAbs all recognized the fusion protein with less specificity, with only 5D4, 5E8 and 8A7 demonstrating significant binding and yielding similar titration curves.

Figure 4A:
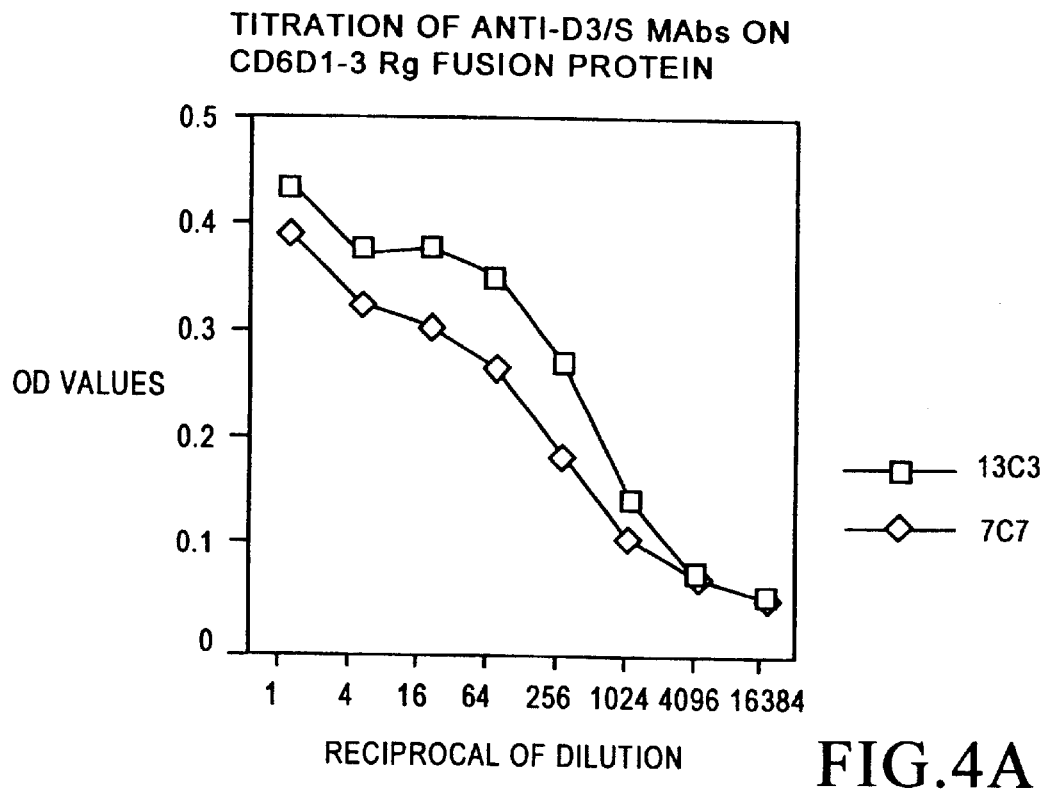
Figure 4B:
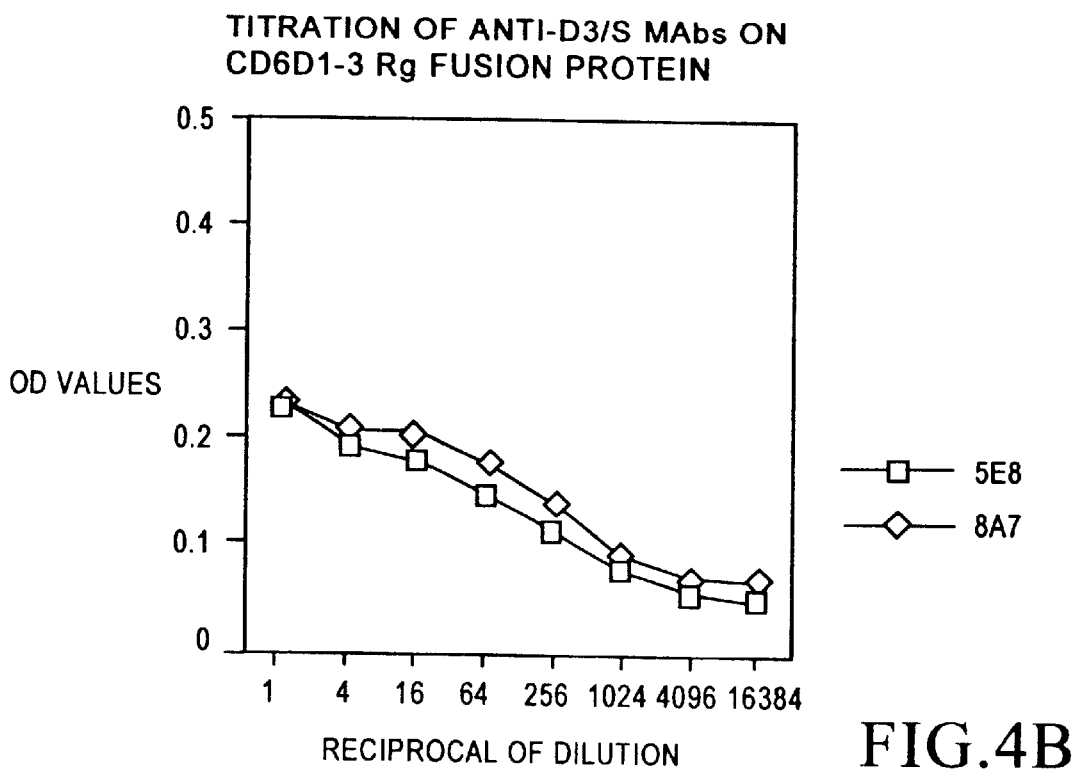
Figure 4C:
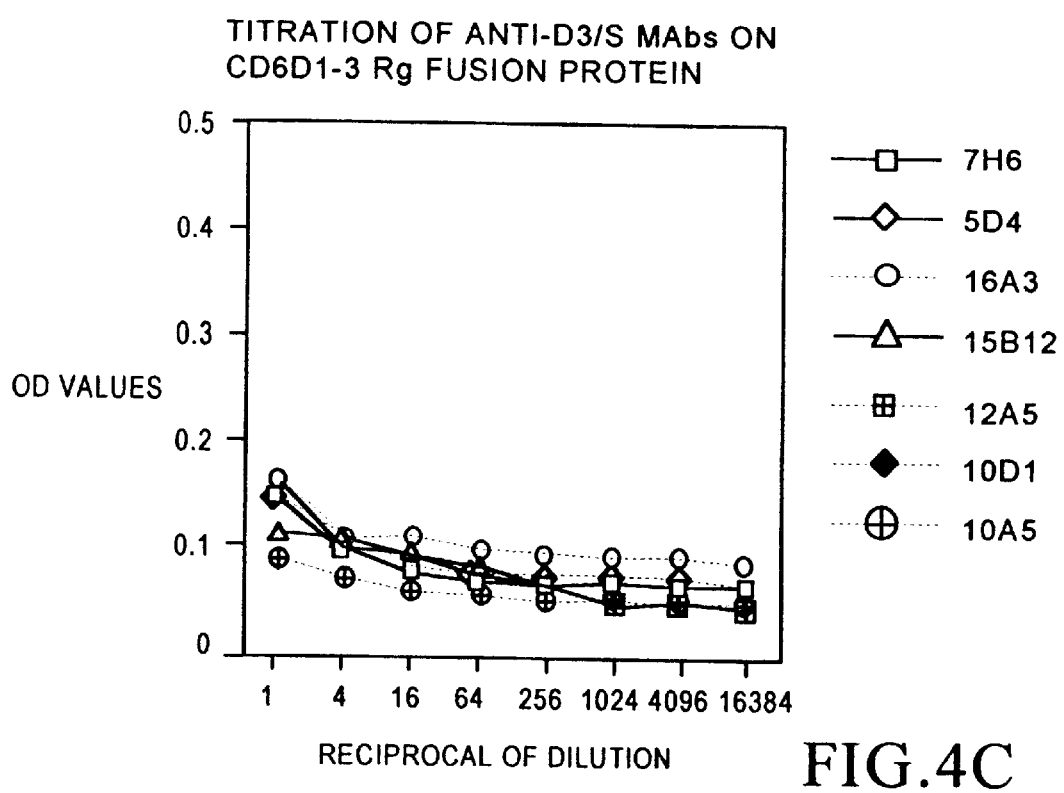
Figure 5A:
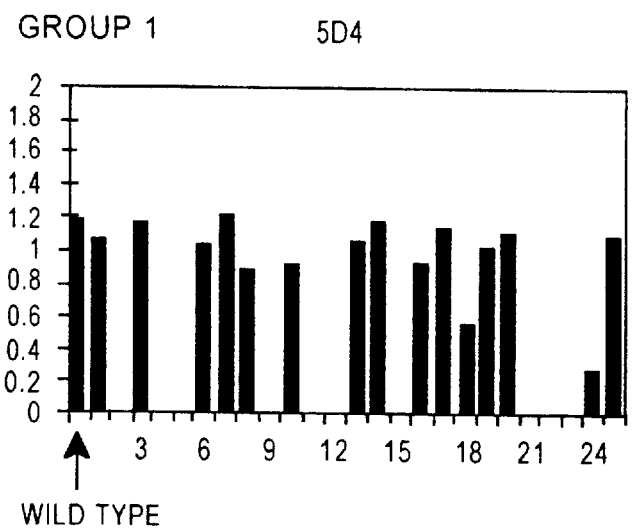
FIGS. 5A–5E and 6A–6F depict ELISA binding assay results for various, exemplary anti-human CD6D3/anti-human CD6S monoclonal antibodies within different CD binding subgroups on wild-type hCD6 SRCR D3 or mutant proteins. Mutants are numbered according to Table 7 on the x-axis. O.D. values are recorded on the y-axis.
Figure 5B:
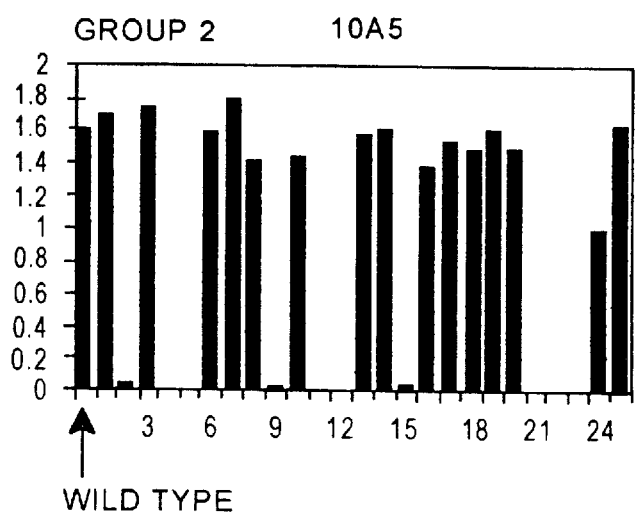
Figure 5C:
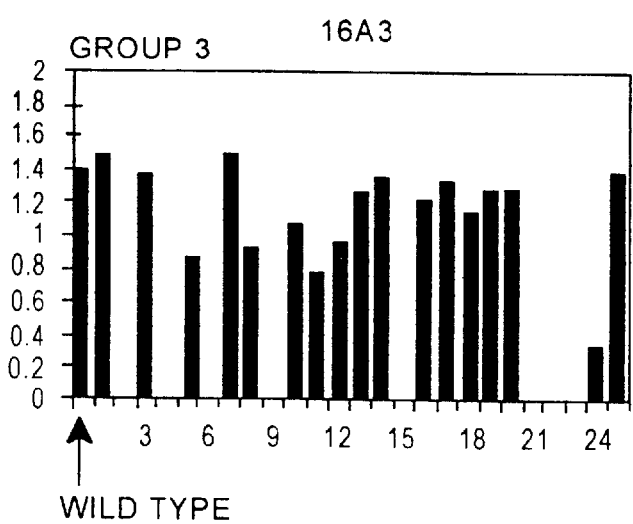
Figure 5D:
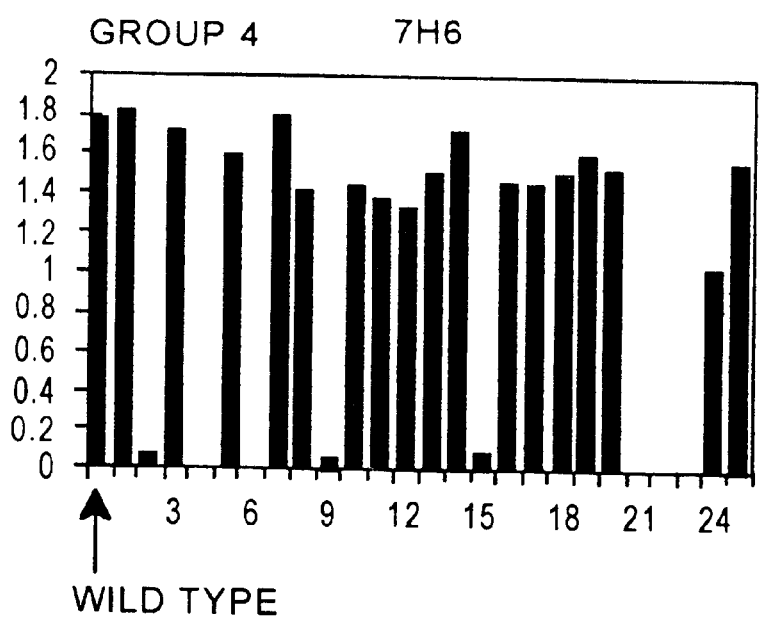
Figure 5E:
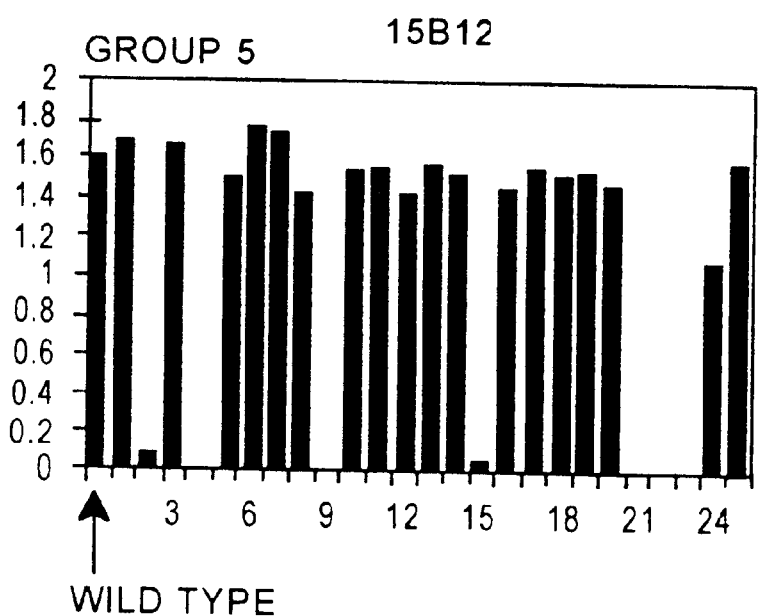
Figure 6A:
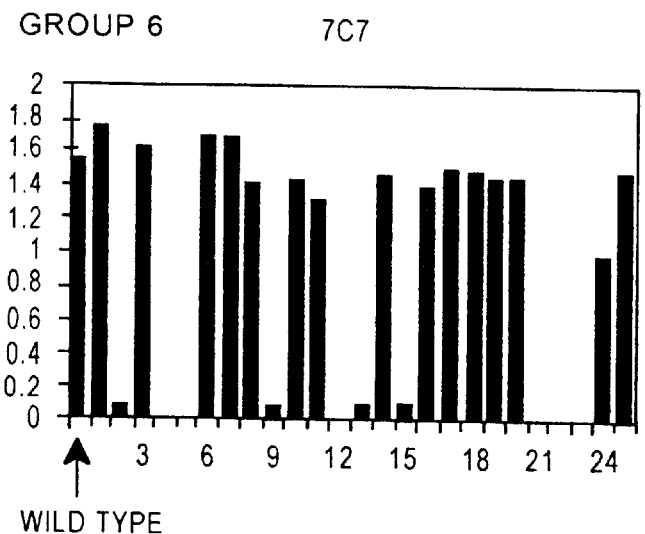
Figure 6B:
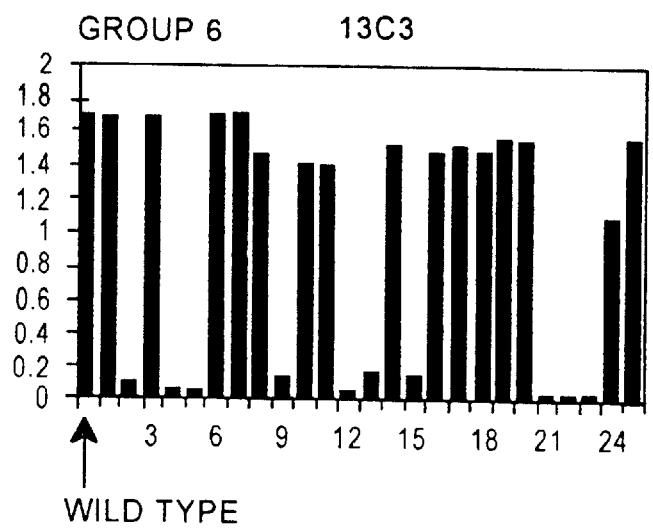
Figure 6C:
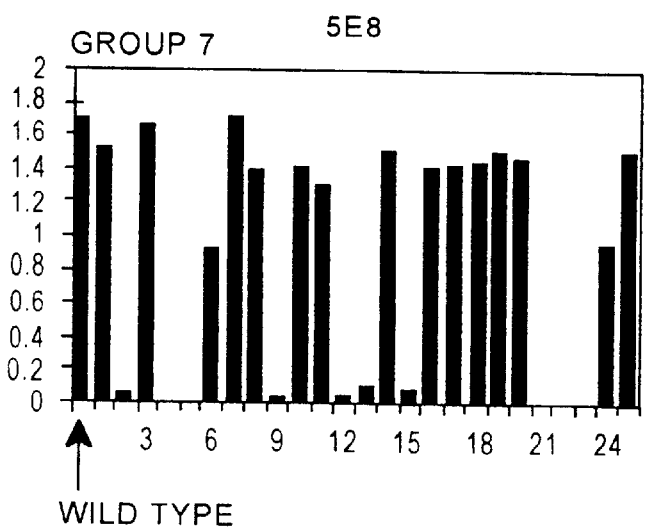
Figure 6D:
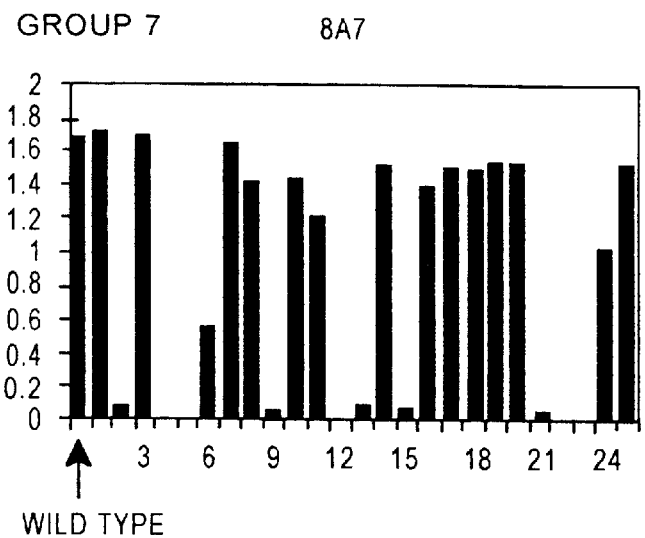
Figure 6E:
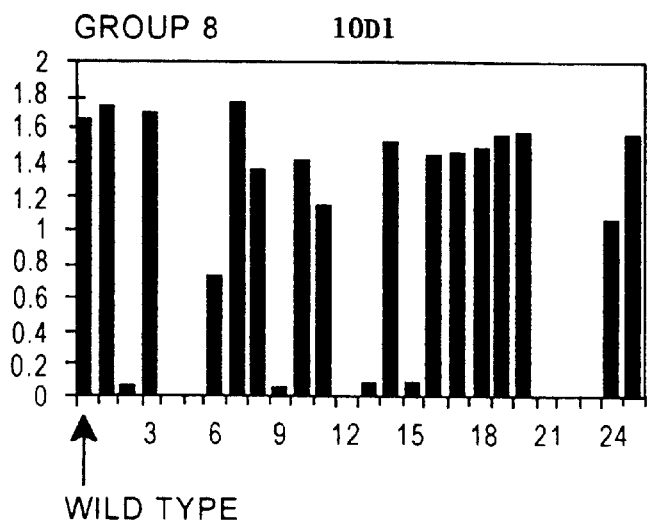
Figure 6F:
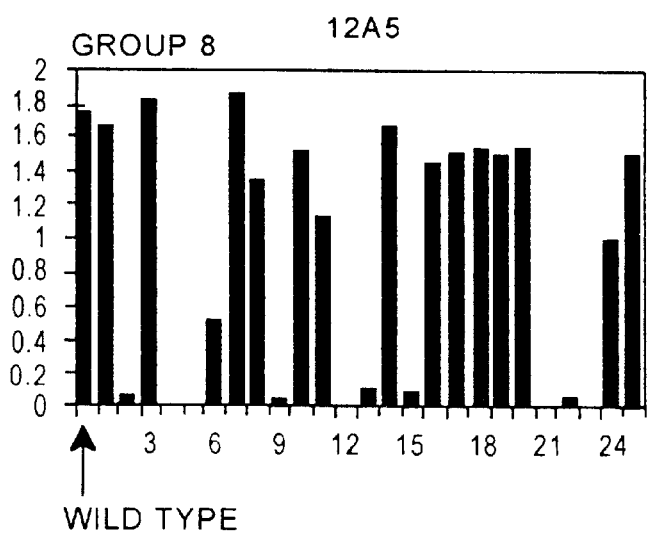
Figure 7A:
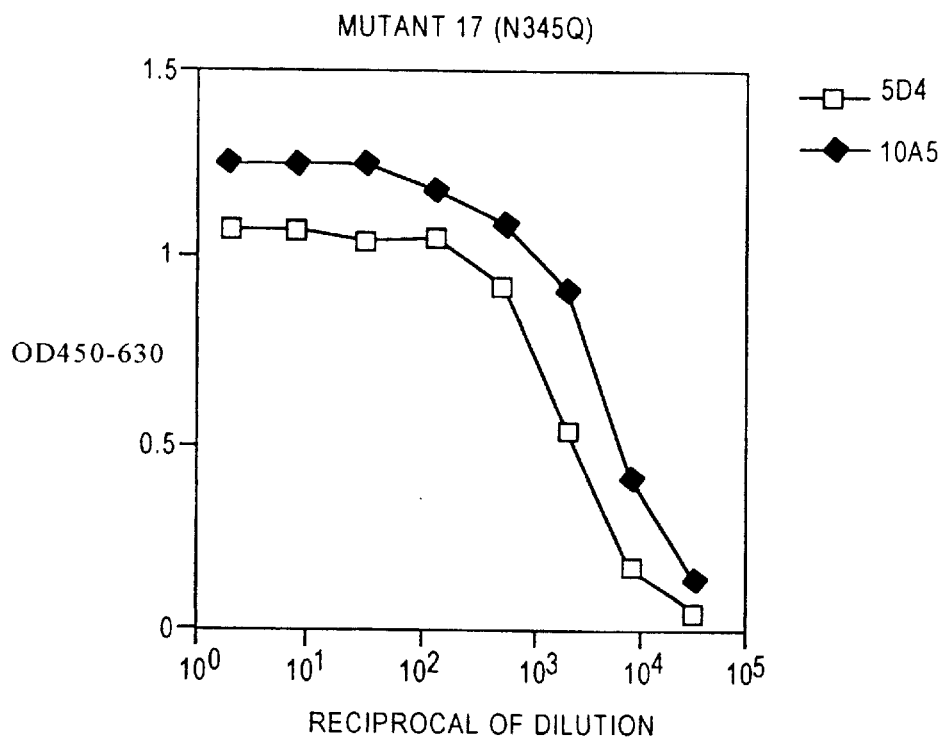
FIGS. 7A and 7B show titration curves at various monoclonal antibody dilutions to mutant hCD6 SRCR D3 proteins.
Figure 7B:
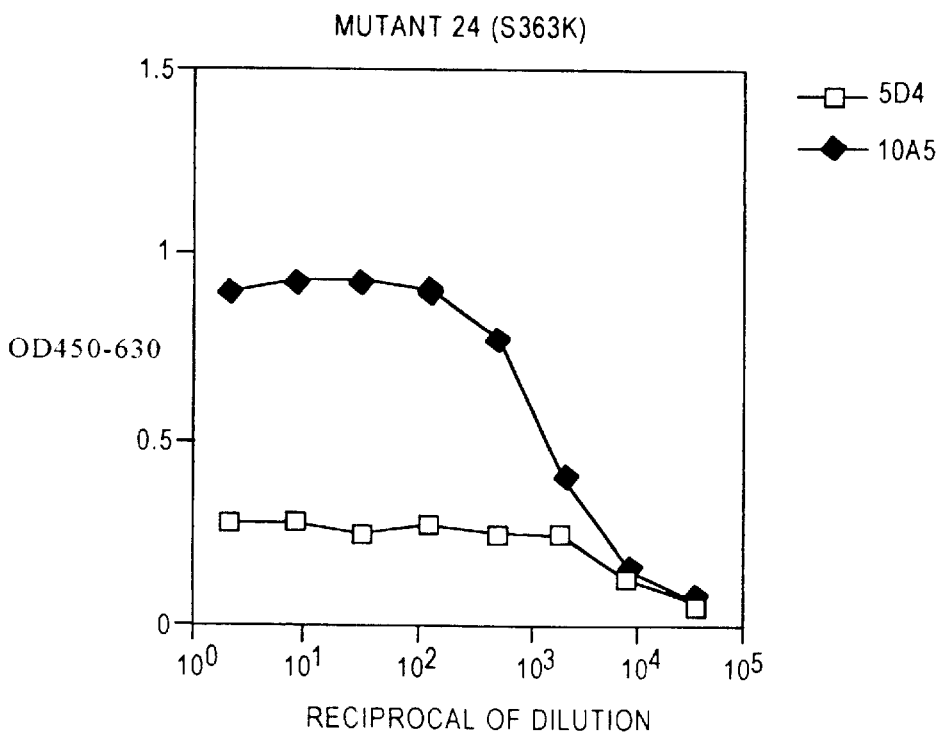

To control for potential bias of the second step reagent for one IgG isotype over another, the assay was repeated using an anti-murine kappa light chain second step reagent (all the mAbs had previously been shown to possess this type of light chain using the IsoStrip test). As shown in FIGS. 4A–4C, mAbs 7C7 and 13C3 again appeared quite similar in their greater recognition of CD6D1-3 Rg. mAbs 5E8 and 8A7 also appeared to group based on their very similar, intermediate recognition of the protein. The other mAbs demonstrated poor binding in this format.

Taken together, these data point to at least five distinct binding subgroups among the anti-D3/S mAbs, which subgroups are characterized by their distinct titration profiles and separated as follows:

Group A—16A3

Group B—7C7, 13C3

Group C—5D4

Group D—5E8, 8A7

Group E—7H6, 10A5, 10D1, 12A5, 15B12

EXAMPLE VI

CD6 Binding Subgroups Among Anti-Human CD6D3/S Antibodies Determined by Mutational Analyses An independent means of assessing epitope specificity for the anti-D3/S mAbs was carried out using mutant CD6D3-S Rg proteins containing a single, or in one case a double, point mutation in the third SRCR domain. More specifically, mAbs 5D4, 10A5, 16A3, 7H6, 15B12, 7C7, 13C3, 5E, 8A7, 10D1, and 12A5 were tested by ELISA and grouped based on their ability to bind to a panel of 25 mutant CD6D3-S fusion proteins. A list of these mutants by mutant number and corresponding notation of original (left) and substituted (right) amino acids at the enumerated residue(s) is provided in Table 7, below.

TABLE 7

CDG SRCR D3 Mutant Proteins

| Mutant | Residue/Mutations |
|---|---|
| 1 | A271R |
| 2 | Q277R |
| 3 | V285E |
| 4 | W286R |
| 5 | E293R |
| 6 | P296R |
| 7 | Q304E |
| 8 | Q304R |
| 9 | S305R |
| 10 | S321K |
| 11 | Y327R |
| 12 | S329R |
| 13 | E333K |
| 14 | N339D |
| 15 | F344R |
| 16 | N345D |
| 17 | N345Q |
| 18 | N346K |
| 19 | N348R |
| 20 | Q352R |
| 21 | S353K |
| 22 | A355D |
| 23 | R357E |
| 24 | S363K |
| 25 | N339D/N345D |

ELISA assays to detect binding activity of the anti-D3/S antibodies as affected by the CD6 mutations specified in Table 7 were generally carried out according to the methods of Bowen et al., supra. Briefly, Immulon 1 plates were coated with donkey anti-human IgG (Jackson) at 1 $\mu$g/ml in carb/bicarb buffer with 50 $\mu$l/well overnight at room temperature. Samples were washed twice with 300 $\mu$l/well PBS (Gibco)/0.05% Tween 20 (Biorad). Blocking was conducted with 100 $\mu$l/well Genetic Systems Specimen Diluent, incubated for 1.5 hours at room temperature, followed by two washes with 300 $\mu$l/well PBS/0.05% Tween 20. Subsequently, 50 $\mu$l/well of CD6 mutant supernatant at 0.5 $\mu$g/ml (diluted in DMEM/10% FBS (Gibco) was added and incubated for 1.5 hours at room temperature, performed in duplicate for each of the mAbs tested. After this incubation step, samples were again washed three times with 300 $\mu$l/well PBS/0.05% Tween 20. Next, 50 $\mu$l/well of anti-CD6 mAb supernatant diluted 1:5 in Genetic Systems Specimen Diluent was added and incubated for 1.5 hours at room temperature. Again, samples were washed four times with 300 $\mu$l/well PBS/0.05% Tween 20. Developing was conducted with 100 $\mu$l/well Genetic Systems Chromagen/Buffered Substrate at 1:100 Chromagen/buffer, incubated about 15 minutes or until blue at room temperature. Reactions were stopped with 100 $\mu$l/well 1N $H_2SO_4$, and Optical Densities (ODs) at 450 and 630 nm were determined.

Results of the ELISA assays for the CD6D3-S point mutants are shown in FIGS. 5A–5E and 6A–6F. Notably, all of the mAbs bound to mutants 1, 3, 7, 8, 10, 14, 16–20, 24, and 25, while none of the mAbs exhibited binding to any of the mutants 2, 4, 9, 15, and 21–23. Group 1 antibodies (exemplified by mAb 5D4) and Group 2 antibodies (exemplified by mAb 10A5) where characterized by their ability to bind to mutant 24 (S363K), with mAb 10A5 exhibiting the strongest binding among members of these two groups when titrated over a broad range of dilutions. As a control to demonstrate that the concentrations of mAb in the hybridoma supernatants were comparable, mAb 5D4 binding to mutant 17 (N345Q) paralleled 10A5 binding.

Additional CD6 binding subgroups were demonstrated by the mutant ELISA assays, from which it was determined that Group 3 antibodies (exemplified by mAb 16A3) and Group 4 antibodies (exemplified by mAb 7H6) did not bind to mutant 6 (P296R). Both Group 3 and Group 4 antibodies recognized mutant 24 (S363K), but when titrated over a broad range of dilutions mAb 16A3 did not bind as well as mAb 7H6. Again, as a control for mAb concentration, both mAbs 16A3 and 7H6 were demonstrated to exhibit similar binding on mutant 25 (N339D/N345D).

Further characterization of CD6 binding subgroups showed that Group 5 antibodies (exemplified by mAb 15B12) were distinguished by their ability to bind all mutant proteins except for those mutants (2, 4, 9, 15, and 21–23) that were not recognized by any of the mAbs tested (FIG. 5E).

Three additional subgroups of anti-D3/S antibodies were confirmed by the ELISA/CD6 mutant assays, which demonstrated that Group 6 antibodies (exemplified by mAbs 7C7 and 13C3), Group 7 antibodies (exemplified by mAbs 5E8 and 8A7) and Group 8 antibodies (exemplified by mAbs 10D1 and 12A5) did not bind to mutants 5, 12 and 13 (FIGS. 6A–6F). Binding to mutant 6 subdivided these groups. Group 7 and Group 8 antibodies did not recognize this mutant as well as did Group 6. Additionally, these mAbs had different binding properties on a hCD6 D3 fusion protein that lacked the stalk region.

Further defined characteristics of the various binding subgroups among the panel of anti-D3/S antibodies tested in the CD6 mutant/ELISA assays are demonstrated by the results shown in FIGS. 5A–5E and 6A–6F. According to these results, binding subgroups can be distinguished to varying levels based on the distinct subgroup binding patterns (e.g., identity and number of mutants bound, and/or levels of binding, e.g., expressed as % of wild-type binding) to the panel of 25 CD6 mutants tested. In addition, the titration analysis on the CD6D1-3 Rg protein (Example V; FIGS. 4A–4C) and the ELISA results on the CD6D3-S point mutants are in good agreement with each other with regard to defining specific binding patterns that characterize CD6 binding subgroups 1–8.

Yet additional data to define differential binding patterns between anti-D3/S binding subgroups is provided by titrational analyses, as exemplified for certain mAbs of the invention by the results shown in FIGS. 7A–7B. These assays were conducted according to the titration assays described above, except that the mAbs were titrated by diluting supernatants in Genetic Systems specimen diluent starting at 1:2 and then serial diluted 1:4. As can be seen from the Figure, these assay data, along with the titration analysis on the CD6D1-3 Rg protein (Example V; FIGS. 4A–4C) and ELISA data for CD6D3-S point mutants, collectively demonstrate that eight binding subgroups are present in the panel of anti-D3/S mAbs tested:

Group 1—5D4

Group 2—10A5

Group 3—16A3

Group 4—7H6

Group 5—15B12

Group 6—7C7, 13C3

Group 7—5E8, 8A7

Group 8—10D1, 12A5

Members of these binding subgroups are particularly useful within the invention, for example, as highly specific binding agents to bind CD6 at discrete epitopic sites and/or with distinct binding characteristics, and to identify and characterize additional binding agents that recognize distinct epitopic sites of CD6 or bind CD6 in a unique manner. In addition, these binding subgroups are further useful as binding agents that exhibit distinct activity for modulating CD6/ALCAM interactions, as well as to identify and characterize other binding agents having distinct activities for modulating CD6/ALCAM interactions. In this regard, certain of the CD6 binding subgoups are expected to recognize distinct epitopic sites within the CD6-D3 and/or CD6-S domains, whereas other subgroups will recognize overlapping epitopic sites, or the same epitopic site with varying affinity or potential for modulating CD6/ALCAM interactions.

EXAMPLE VII
Identification and Characterization of Antibodies Specific for the Second SRCR Domain of CD6

Figure 8A:
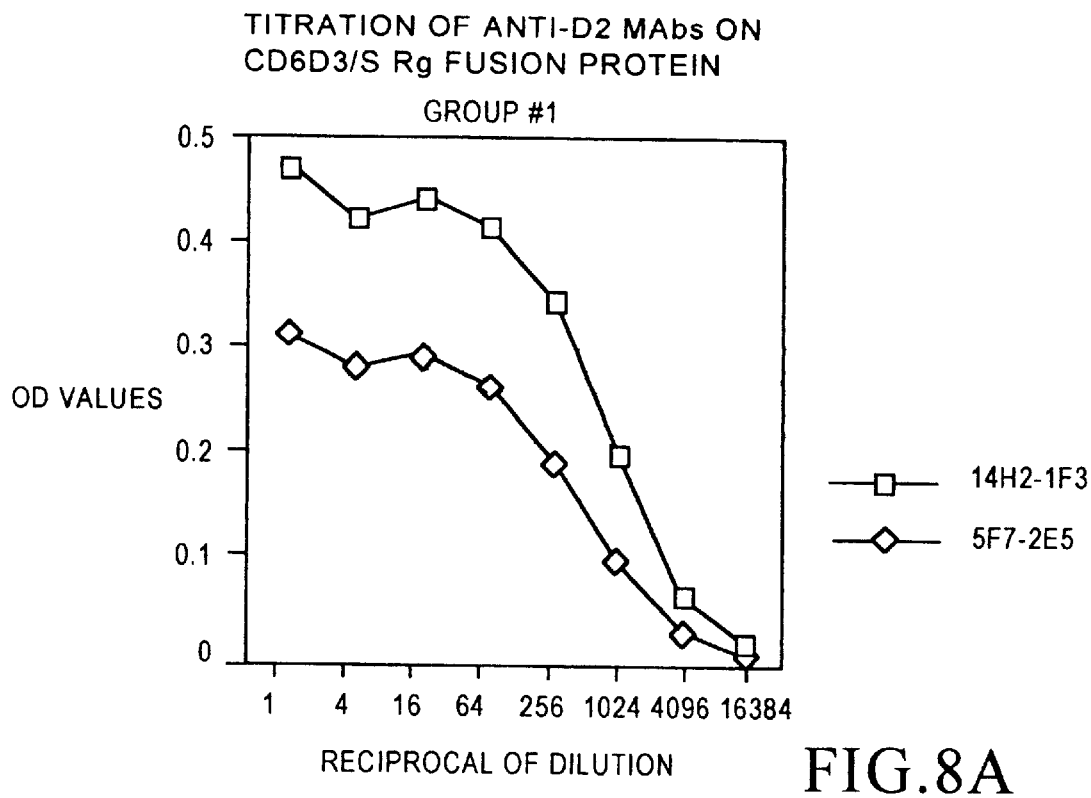
FIGS. 8A and 8B depict titration curves for exemplary anti-human CD6D2 monoclonal antibodies on CD6D3/S Rg fusion protein.
Figure 8B:
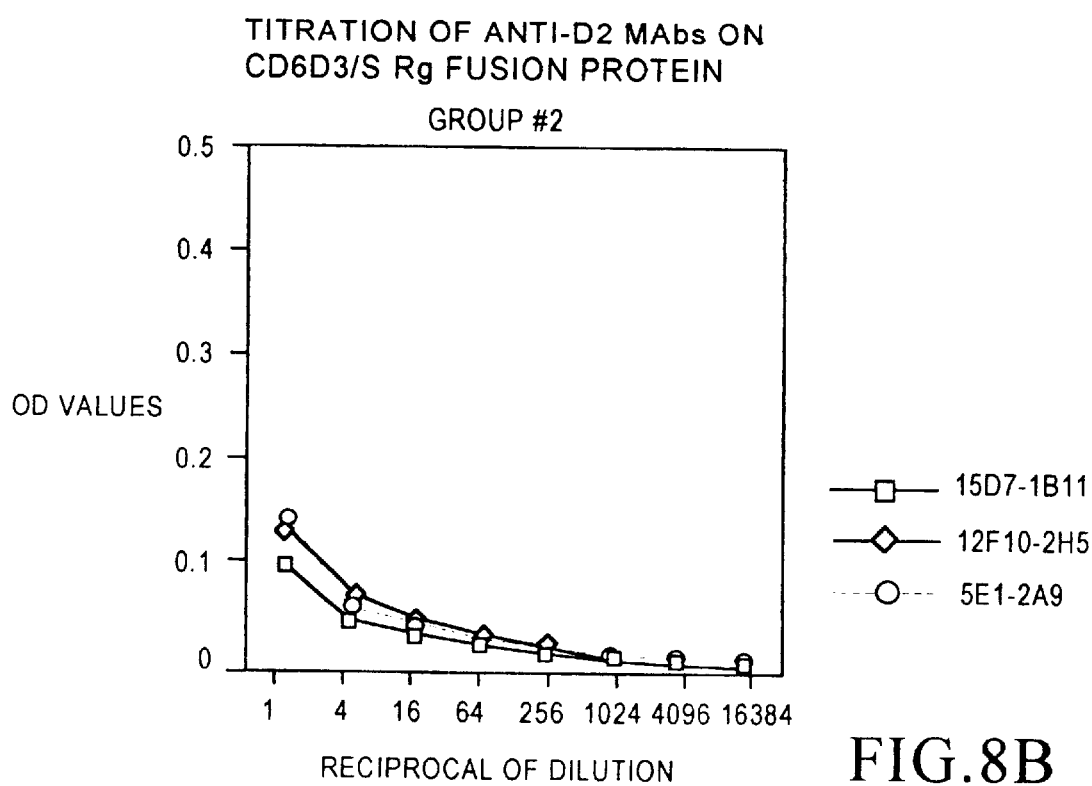

Following evaluation of domain specificity and cloning of the more potent blocking master wells of CD6/ALCAM interaction, all remaining master well supernatants were subjected to ELISA based domain specificity analysis. Results of these tests identified a number of supernatants whose reactivity profiles on the fusion protein panel suggested that they contained an antibody directed against the second SRCR domain of CD6 (CD6D2). Representative results of several such wells are shown in Table 8, below. All demonstrated reactivity with CD6 Rg, CD6D2-S Rg, CD6D1-2 Rg and most importantly, CD6D2 Rg. Interestingly, four of the six examples reacted poorly with the CD6D1-3 Rg protein, again suggesting the likelihood of structural integrity problems as was noted earlier with the anti-D3/S antibodies. The H6-2.10A5 supernatant also demonstrated the presence of a second antibody directed against the D3/S domains of CD6.

earlier. Supernatants from clones were screened by ELISA on the CD6D2 Rg fusion protein with the exception of clones from H6-2.10A5 which were also screened on the CD6D3-S Rg protein. Anti-CD6D2 Rg clones were successfully isolated from each of the master wells except for H6-2.10A5. Anti-CD6D3-S Rg clones were, however, isolated from the latter master well. Results of a full CD6 fusion protein domain specificity test by ELISA for representative examples of anti-CD6D2 Rg clones are shown in Table 9. Similar data for the anti-CD6D3-S Rg clones is presented in Table 4, above, as previously discussed. All the anti-CD6D2 Rg antibodies reacted well with any fusion protein containing the second SRCR domain of CD6 and none recognized the irrelevant CD40 Rg protein. On this basis, a domain specificity assignment for these mAbs to the second SRCR domain (i.e., anti-D2 mAbs) was concluded. It is interesting to note, however, that two of the mAbs (H6-2.5F7 and H6-2.14H2) reacted weakly and consistently with the CD6D3-S Rg protein while the others did not. Reasons for this were unclear but the observation did provide evidence that at least two different epitopes were recognized by the anti-D2 mAbs and that therefore two subgroups of anti-D2 mAbs had been isolated; group 1 comprised of H6-2.5F7 and H6-2.14H2 and group 2 comprised of H6-1.5E1, H6-1.12F10 and H6-1.15D7. In support of this conclusion, a full ELISA based titration of anti-D2 supernatants on the CD6D3-S Rg protein was performed. As shown in FIGS. 8A–8B, group 1 mAbs reacted with this protein in a saturable, titratable manner while the group 2 mAbs barely recognized the protein. These results were not due to a greater concentration of antibody in the group 1 supernatants as an anti-mouse Ig sandwich ELISA indicated higher immunoglobulin levels in the group 2 supernatants compared to the group 1 supernatants.

TABLE 8

REACTIVITY OF SELECTED MASTER WELL SUPERNATANTS WITH TRUNCATED CD6 RG FUSION PROTEINS

| MAb | CD6 Rg | CD6D2-S Rg | CD6D3-S Rg | CD6D1-2 Rg | CD6D2 Rg | CD6D1-3 Rg | CD40 Rg |
|---|---|---|---|---|---|---|---|
| H6-1.5E1 | 1.49 ± 0.04 | 1.07 ± 0.00 | 0.01 ± 0.00 | 0.78 ± 0.03 | 1.32 ± 0.01 | 0.13 ± 0.02 | 0.02 ± 0.00 |
| H6-1.12F10 | 0.97 ± 0.02 | 0.41 ± 0.00 | 0.01 ± 0.00 | 0.45 ± 0.00 | 0.73 ± 0.00 | 0.05 ± 0.00 | 0.01 ± 0.00 |
| H6-1.15D7 | 1.51 ± 0.05 | 1.22 ± 0.03 | 0.02 ± 0.01 | 0.89 ± 0.08 | 1.45 ± 0.04 | 0.17 ± 0.01 | 0.02 ± 0.01 |
| H6-2.5F7 | 1.69 ± 0.02 | 1.61 ± 0.04 | 0.03 ± 0.00 | 1.52 ± 0.06 | 1.56 ± 0.06 | 1.97 ± 0.01 | 0.01 ± 0.00 |
| H6-2.10A5 | 1.90 ± 0.06 | 1.88 ± 0.03 | 1.81 ± 0.01 | 1.75 ± 0.02 | 1.82 ± 0.06 | 0.02 ± 0.00 | 0.00 ± 0.00 |
| H6-2.14H2 | 1.72 ± 0.04 | 1.69 ± 0.01 | 0.05 ± 0.00 | 1.56 ± 0.08 | 1.72 ± 0.02 | 1.20 ± 0.01 | 0.01 ± 0.00 |
| Mu anti-hCD6 Polyclonal Serum | 1.94 ± 0.02 | 1.66 ± 0.02 | 1.56 ± 0.06 | 1.81 ± 0.00 | 1.63 ± 0.01 | 1.64 ± 0.03 | 0.03 ± 0.00 |

Bold Print = Positive = $OD_{450/630} \geq 0.15$

Specific antibody producing hybridomas from each of the master wells shown in Table 8 were cloned as described

TABLE 9

REACTIVITY OF ANTI-CD6 DOMAIN 2 MAbs WITH TRUNCATED CD6 Rg FUSION PROTEINS

| MAb | CD6 Rg | CD6D2-S Rg | CD6D3-S Rg | CD6D1-2 Rg | CD6D2 Rg | CD6D1-3 Rg | CD40 Rg |
|---|---|---|---|---|---|---|---|
| H6-1.5E1 | 2.04 ± 0.03 | 2.07 ± 0.03 | 0.03 ± 0.00 | 1.88 ± 0.01 | 1.81 ± 0.06 | 1.46 ± 0.03 | 0.01 ± 0.00 |
| H6-1.12F10 | 1.87 ± 0.01 | 1.79 ± 0.13 | 0.04 ± 0.01 | 1.71 ± 0.04 | 1.62 ± 0.03 | 1.20 ± 0.03 | 0.02 ± 0.01 |
| H6-1.15D7 | 2.03 ± 0.01 | 2.05 ± 0.01 | 0.04 ± 0.01 | 1.95 ± 0.01 | 1.90 ± 0.01 | 1.70 ± 0.04 | 0.01 ± 0.00 |
| H6-2.5F7 | 2.03 ± 0.05 | 1.97 ± 0.00 | 0.21 ± 0.02 | 1.97 ± 0.04 | 1.91 ± 0.01 | 1.95 ± 0.01 | 0.01 ± 0.00 |
| H6-2.14H2 | 2.05 ± 0.01 | 1.99 ± 0.04 | 0.34 ± 0.00 | 1.96 ± 0.02 | 1.90 ± 0.02 | 1.94 ± 0.04 | 0.01 ± 0.00 |
| Mu anti-hCD6 Polyclonal Serum | 2.11 ± 0.02 | 1.97 ± 0.01 | 1.84 ± 0.03 | 2.01 ± 0.06 | 1.89 ± 0.03 | 1.94 ± 0.04 | 0.05 ± 0.00 |

Bold Print = Positive = $OD_{450/630} \geq 0.15$

Clonal supernatants containing these five mAbs were next evaluated for binding to CD6+ cells and capacity to block ALCAM Rg binding to CD6+ cells as described earlier for commercial/workshop anti-SRCR domain 1 mAbs and fusion master well supernatants. As shown in Table 6, all five mAbs stained CD6+ HPB-ALL cells at comparable levels to that seen with anti-D1 and anti-D3/S mAbs. In contrast to anti-D3/S mAbs, anti-D2 mAbs were unable to block the interaction of ALCAM Rg with HPB-ALL cells and in fact appeared to actually enhance this receptor/ligand interaction as was earlier noted for some anti-D1 mAbs. There were no apparent differences in binding and blocking capabilities between group 1 and group 2 anti-D2 mAbs.

Murine IgG subclassification of the five anti-D2 mAbs was determined using the IsoStrip test described above. All five mAbs were determined to have the $IgG_1$ isotype.

Although the foregoing invention has been described in some detail by way of illustration and example for purposes of clarity of understanding, those with ordinary skill in the art will appreciate that other embodiments and variations of the invention are possible which employ the same inventive concepts described above. Therefore, the invention is not to be limited by the above disclosure, but is to be determined in scope by the claims which follow.

What is claimed is:

1. An anti-human CD6 antibody that binds specifically to human CD6 scavenger receptor cystine-rich (SRCR) domain 3 (CD6D3) or human CD6 stalk domain (CD6S) and inhibits activated leukocyte cell adhesion molecule (ALCAM) binding to CD6.

2. The anti-human CD6 antibody according to claim 1, which is an anti-CD6D3 or anti-CD6S monoclonal antibody or fragment thereof.

3. The anti-human CD6 antibody according to claim 2, wherein the antibody or fragment thereof specifically binds a CD6 domain 3-stalk region-Ig protein fusion (CD6D3-S Rg).

4. The anti-human CD6 antibody according to claim 2, wherein the monoclonal antibody is a humanized monoclonal antibody.

5. The anti-human CD6 antibody according to claim 4, wherein the humanized monoclonal antibody is a human-mouse chimeric antibody comprising a mouse variable domain operably linked to a human constant domain.

6. The anti-human CD6 antibody according to claim 4, wherein the monoclonal antibody has a CD6D3-S mutant protein binding profile comprising:

A) binding to CD6D3-S P296R Rg, and CD6D3-S E333K Rg, but not to CD6D3-S E293R Rg and CD6D3-S S329R Rg;

B) binding to CD6D3-S E293R Rg, CD6D3-S S329R Rg, and CD6D3-S E333K Rg, but not to CD6D3-S P296 Rg;

C) binding to CD6D3-S E293R Rg, CD6D3-S P296R Rg, CD6D3-S S329R Rg, and CD6D3-S E333K Rg; or D) binding to CD6D3-S P296R Rg, but not to CD6D3-S E293R Rg, CD6D3-S S329R Rg, and CD6D3-S E333K Rg.

7. The anti-human CD6 antibody according to claim 6, wherein the monoclonal antibody is a modified immunoglobulin that exhibits substantial amino acid sequence identity to, and retains substantially the same CD6D3-S mutant protein binding profile, as profile A, B, C or D.

8. The anti-human CD6 antibody according to claim 6, wherein the monoclonal antibody of profile A has the CD6D3-S mutant protein binding profile of a Group 1 (ATCC HB12291) antibody or Group 2 (ATCC HB12289) antibody.

9. The anti-human CD6 antibody according to claim 8, wherein the monoclonal antibody of profile A is produced by the hybridoma deposited with ATCC designated ATCC HB12291 or ATCC HB12289.

10. The anti-human CD6 antibody according to claim 6, wherein the monoclonal antibody of profile B has the CD6D3-S mutant protein binding profile of a Group 3 (ATCC HB 12296) antibody or Group 4 (ATCC HB 12292) antibody.

11. The anti-human CD6 antibody according to claim 10, wherein the monoclonal antibody of profile B is produced by the hybridoma deposited with ATCC designated ATCC HB12296 or ATCC HB12292.

12. The anti-human CD6 antibody according to claim 6, wherein the monoclonal antibody of profile C has the CD6D3-S mutant protein binding profile of a Group 5 (ATCC HB12293) antibody.

13. The anti-human CD6 antibody according to claim 12, wherein the monoclonal antibody of profile C is produced by the hybridoma deposited with ATCC designated ATCC HB 12293.

14. The anti-human CD6 antibody according to claim 6, wherein the monoclonal antibody of profile D has the CD6D3-S mutant protein binding profile of a Group 6 (ATCC HB 12288) antibody, a Group 7 (ATCC HB12295) antibody, or a Group 8 (ATCC HB12290) antibody.

15. The anti-human CD6 antibody according to claim 14, wherein the monoclonal antibody of profile D is produced by the hybridoma deposited with ATCC designated ATCC HB 12288, ATCC HB 12295, or ATCC HB12290.

16. The anti-human CD6 antibody according to claim 1, wherein the antibody is a single chain antibody, an $F(ab')_2$, F(ab'), Fv fragment, a single heavy chain or a single light chain.

* * * * *